United States Patent [19]

Culver

[11] 4,407,299

[45] Oct. 4, 1983

[54] BRAIN ELECTRICAL ACTIVITY MAPPING

[75] Inventor: Norman D. Culver, Spotswood, N.J.

[73] Assignee: The Children's Medical Center Corporation, Boston, Mass.

[21] Appl. No.: 264,031

[22] Filed: May 15, 1981

[51] Int. Cl.³ .............................................. A61B 5/04
[52] U.S. Cl. .................................... 128/731; 128/732
[58] Field of Search ............................... 128/731–733, 128/905

[56] References Cited

U.S. PATENT DOCUMENTS

| | | | |
|---|---|---|---|
| 2,928,189 | 3/1960 | Molner et al. | 35/22 |
| 3,696,808 | 10/1972 | Roy et al. | 128/2.1 B |
| 3,705,297 | 12/1972 | John | 235/150.53 |
| 3,706,308 | 12/1972 | John et al. | 128/2.06 R |
| 3,707,147 | 12/1972 | Sellers | 128/2.06 G |
| 3,717,141 | 2/1973 | Krohn et al. | 128/2.66 R |
| 3,780,724 | 12/1973 | John | 128/2.1 B |
| 3,799,146 | 3/1974 | John et al. | 128/2.1 B |
| 3,901,215 | 8/1975 | John | 128/2.1 B |
| 4,094,307 | 6/1978 | Young | 128/2.1 B |
| 4,171,696 | 10/1979 | John | 128/731 |

OTHER PUBLICATIONS

Duffy et al.; Significance Probability Mapping: An Aid in the Topographic Analysis of Brain Electrical Activity; EEG and Clin. and Neurophysiology, 1981, pp. 1–8.

Duffey et al.; "Quantification of Focal Abnormalities in Beam Data by Grid Sector Analysis".
Duffy et al., "Brain Electrical Activity Mapping (BEAM): A Method for Extending the Clinical Utility of EEG and Evoked Potential Data," Annals of Neurology, vol. 5, No. 4 (Apr. 1979) pp. 309–321.
Duffy et al., "Dyslexia: Regional Differences in Brain Electrical Activity by Typographic Mapping"; Annals of Neurology; vol. 7, No. 5, 5–1980, pp. 412–420.
Duffy et al.; "Dyslexia: Automated Diagnosis by Computerized Classification of Brain Electrical Activity"; Annals of Neurology; vol. 7, No. 5, 5–1980, pp. 421–428.

Primary Examiner—Kyle L. Howell
Assistant Examiner—Angela D. Sykes

[57] ABSTRACT

Information on brain electrical activity is derived from electrical-activity transducers spaced apart over the skull, the information is processed into a time sequence of matrices having elements representing the responses of the transducers, a succession of overlapping running-average matrices is generated each corresponding to an average of a plurality of the matrices in the time sequence, and the running-average matrices are displayed as a sequence of topographic maps. Expanded display matrices are generated from the data matrices by adding new matrix elements using three-point linear interpolation based on pre-stored coefficients corresponding to the location of each new matrix element with respect to the three closest transducer locations.

4 Claims, 32 Drawing Figures

Fig 14

EP DATA e.g. [waveform diagram: 0 MSEC, 4 MSEC ... 508 MSEC; CH1...CH20; To → Tn; 133]

AVERAGED EVOKED RESPONSE SUMS OVER TIME-GIVING AN AVERAGED RESPONSE WAVEFORM SET

Fig 15

FFT DATA e.g. [diagram: .5Hz, 1Hz, 32Hz; CH1...CH20; SUMS 130, 131; SUM SQ 132]

FFT ENSEMBLE CONSISTING OF:
1. POWER SPECTRAL DENSITY SUMS AND SUMS SQUARED
2. NORMALIZED PSD SUMS
3. COEFFICIENT OF VARIATION SUMS

Fig 16 e.g. [diagram: 1ST 2 SEC SEGMENT ANALYZED, 2ND 2 SEC SEGMENT ANALYZED; .5Hz, 32Hz; CH1 SINE/CH1 COS ... CH20 SINE/CH20 COS]

INDIVIDUAL FFT'S CONSISTING OF:
1. SINE & COSINE COEFFICIENTS
2. NORMALIZED SINE AND COSINE COEFFICIENTS

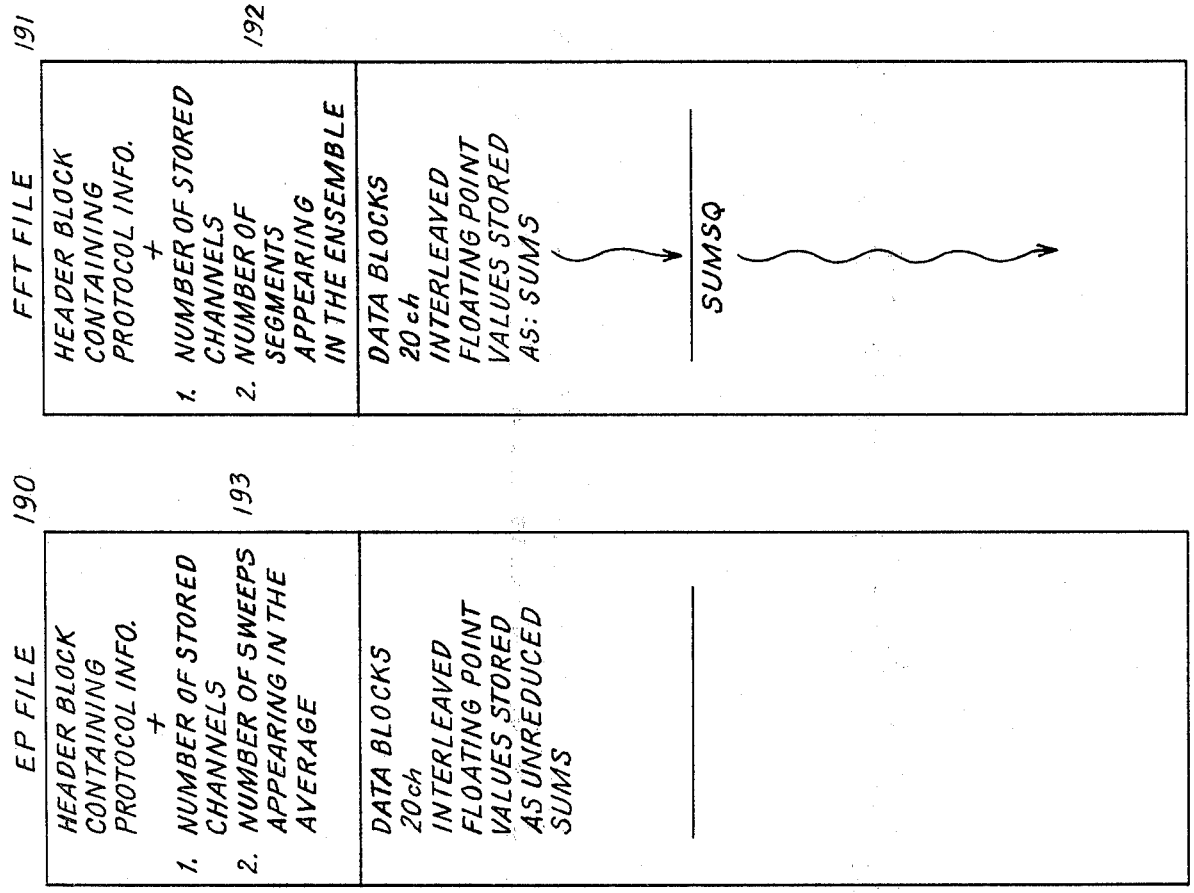

BRAIN ELECTRICAL ACTIVITY MAPPING

BACKGROUND OF THE INVENTION

This invention relates to analysis of brain electrical activity and diagnosis of brain disorders.

Traditional electro-encephalographic (EEG) techniques of analyzing brain electrical activity to diagnose brain dysfunction require the skilled neurophysiologist to observe and distinguish time and frequency related characteristics of many channels of voltage waveforms derived from an individual's brain and to determine, largely from memory, differences between that individual's waveforms and waveforms characteristic of a normalized population. The process necessarily fails to take account of many subtle but potentially useful pieces of information contained in the analyzed data.

Signal averaged sensory evoked potential (EP) transient responses have also been used as a source for brain electrical activity analysis, but large amounts of useful information contained in such transient response waveforms have traditionally been disregarded because of the difficulty of visualizing the inter-relationship over time of many channels of such information.

SUMMARY OF THE INVENTION

The invention features, in one aspect, generating topographic displays of information on electrical activity of the brain produced at a plurality of transducers on the skull; generating a time sequence of matrices of electrical activity at successive points in time; generating a set of running-average matrices each of which is the average of a group of successive matrices; and display means for displaying the running-average matrices as topographic maps in time sequence at a variable rate.

The invention features, in another aspect, generating a topographic display of information on electrical activity of the brain produced at a plurality of transducers on the skull; sampling and storing the information in matrices corresponding to successive time frames; processing the matrices to generate one or more processed matrices; interpolating to form additional matrix elements between the elements representing the transducer locations, by storing three predetermined interpolation coefficients for each interpolated element, and determining the values of the interpolated elements by three-point linear interpolation from the coefficients and the values of the three closest transducer locations; and displaying the expanded matrices or topographic maps.

The ability to generate a running-average of said display matrices improves the smoothness of the displayed sequence. The three-point linear interpolation provides visually smooth topographic maps and accurately reflects the actual relationship of electrical activities at different points on the brain.

In preferred embodiments, the invention features interpolating to form additional matrix elements between the transducer points; the interpolation can be three-point interpolation, particularly three-point linear interpolation to the values of the three closest transducers; the number of transducers can be in the range of 10 to 200; and the number of picture elements is at least 5 times the number of transducers. The expansion of a matrix of a small number of points to a display matrix of a large number of points significantly improves the smoothness, readability and utility of the resulting topographic displays.

BRIEF DESCRIPTION OF THE DRAWINGS

FIG. 14 is a data file format diagram of signal averaged EP data.

FIG. 15 is a data file format diagram of FFT ensemble data.

FIG. 16 is a data file format diagram of individual FFT data.

FIG. 17 is a data file format diagram of an EP file.

FIG. 18 is a data file format diagram of an FFT file.

DESCRIPTION OF THE PREFERRED EMBODIMENT

We now turn to a description of the preferred embodiment.

System Organization and Software

Figure 1:
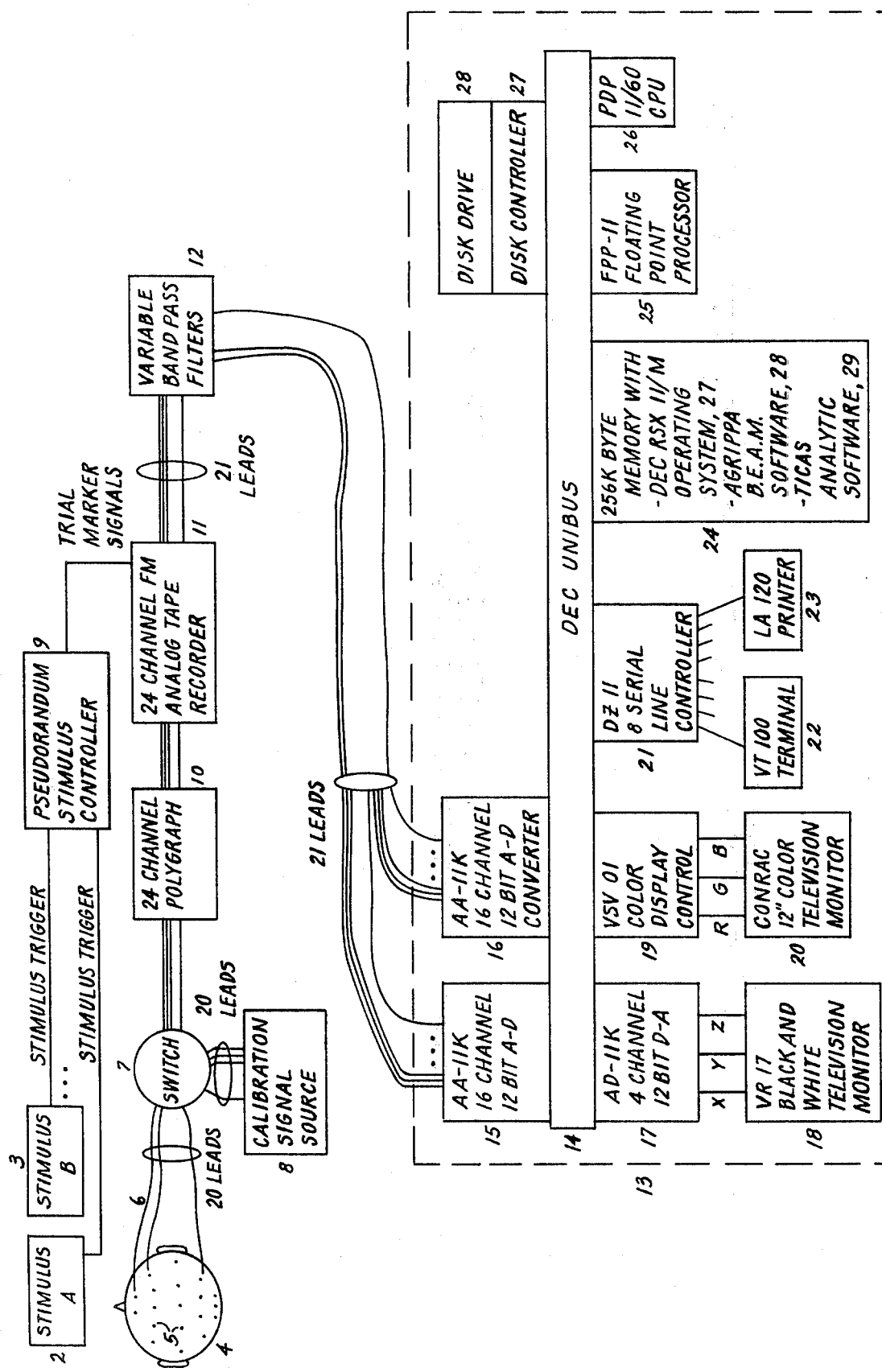
FIG. 1 is a block diagram of the BEAM system.

FIG. 1 illustrates the components of a brain electrical activity mapping system. Twenty electrodes 5 (e.g., Grass gold cup) are attached to subject's skull 4 in a conventional international 10-20 format. Twenty leads 6 from electrodes 5 are connected through switch 7 to conventional 24-channel polygraph 10 (e.g., Grass 8-24D), which contains parallel variable gain differential amplifiers and strip chart recorders. Calibration signal source 8, an A.C. generator, is also connected through switch 7 to polygraph 10. Stimulus A 2 (e.g., Grass Model PS1 strobe light) and stimulus B 3 (e.g., click generator) present stimuli to the subject under the control of pseudorandom stimulus controller 9, which also provides pre-stimulus and stimulus trial marker signals (5 volt spikes) of opposite polarity to one of the input channels to 24-channel FM analog tape recorder 11 (e.g., Honeywell 5600E). In other embodiments, recorder 11 is eliminated and polygraph 10 is connected directly to filter 12 for real-time loading of data. The 21 active outputs of recorder 11 are connected to the inputs of 21 parallel variable band pass filters 12 (e.g., Butterworth filters; EEG Associates Mark 4×24) having variable gain controls. The 21 outputs of filters 12 are connected to 21 of the input terminals of two 16-channel, 12-bit analog-to-digital converters 15, 16 (Digital Equipment Corporation AA-11K), which comprise part of digital computer 13 (Digital Equipment Corporation PDP 11/60). Analog-to-digital converters 15, 16 are attached to data bus 14 (Digital Equipment Corporation Unibus). Also attached to data bus 14 are 4-channel, 12-bit digital-to-analog converter 17 (Digital Equipment Corporation AD-11K) whose three outputs control black and white television monitor 18 (Digital Equipment Corporation VR 17) for waveform displays; color display control 19 (Digital Equipment Corporation VSV 01) whose three outputs control 12" color television monitor 20 (CONRAC) for topographic displays; 8 serial line controller 24 (Digital Equipment Corporation DZ 11) two outputs of which control interactive keyboard and video character display terminal 22 (Digital Equipment Corporation VT 100) and printer 23 (Digital Equipment Corporation LA 120); 256K byte memory 24 containing operation system software 27 (Digital Equipment Corporation RSX 11/M), BEAM software 28 (Agrippa Data Systems), and analytic software 29 (TICAS; University of Arizona); floating point processor 25 (Digital Equipment Corporation FPP-11); central processing unit 26 (Digital Equipment Corporation PDP 11/60); and disk controller 27 controlling at least one disk drive 28.

Software Description

Figure 2:
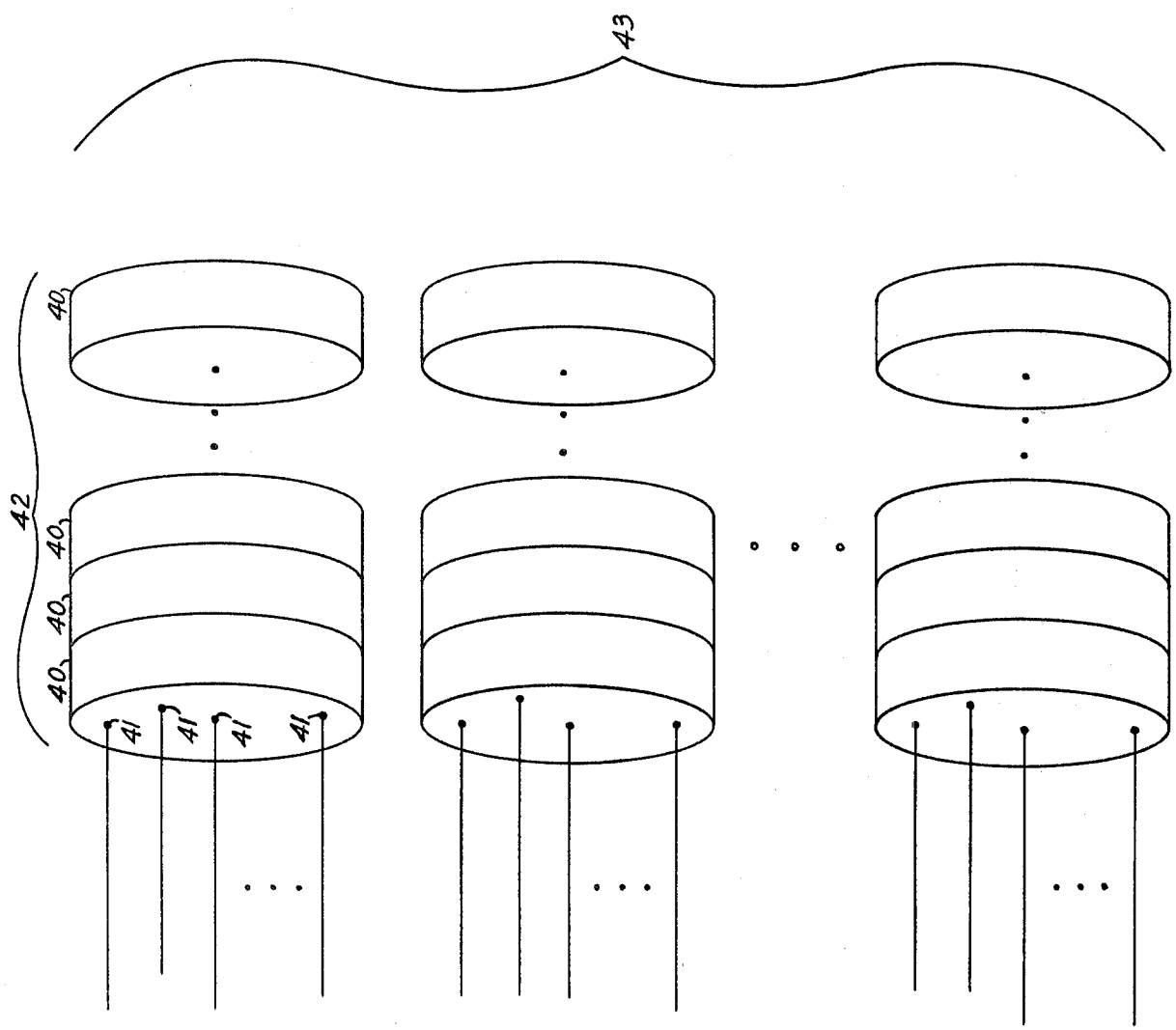
FIG. 2 is a representation of the organization of samples of data in the brain electrical activity mapping system.
Figure 3:
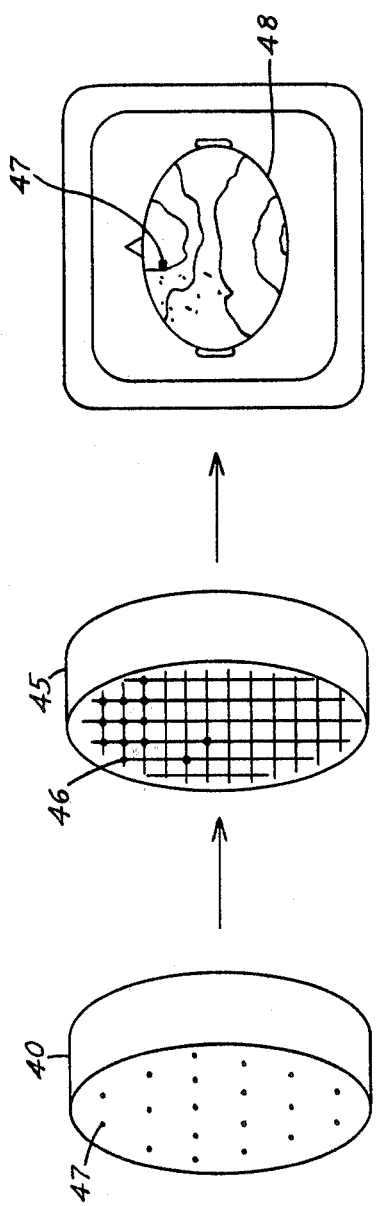
FIG. 3 is a representation of the formation of a topographic display from a frame of data in the brain electrical activity mapping system.

In general, the brain electrical activity mapping system creates color topographic displays reflecting brain electrical activity using, as input, continuous electrical waveforms recorded from a number of points on the skull. The color topographic displays consist of discrete matrices of a large number of display points (also called pixels), each of which has a color of intensity or other visible characteristic which indicates a certain value or values at the location of that point analogous to a point on the skull. In order to generate discrete topographic display matrices having many thousands of display points from continuous analog waveforms at a limited, e.g. 20, number of points on the skull, the brain electrical activity mapping system, as illustrated in FIG. 2, converts the data to digital form and generates discrete sample frames 40, each sample or frame initially comprising 20 recorded values 41 from 20 channels of information. The system treats related groups of samples 40 as segments 42. In the case of EP data, for example, a segment would consist of a series of frames or samples, each 4 milliseconds in length, the series together representing one transient response sequence from the beginning of a pre-stimulus period to the end of the post-stimulus transient response. In the case of steady-state EEG data, a segment would consist of 2 seconds of data divided into 256 samples. A spectral analysis of the EEG data then produces 256 samples, each of which reflects the energy level in a small, e.g. ½ Hz, energy band and a segment consists of the entire series of 256 spectral samples. For signal averaging purposes, the system considers a set of segments together, e.g., 500 segments each representing a transient response to a given stimulus. The 500 segments taken together are known as an ensemble 43. Frames of data can be raw data or data which has been processed or transformed by the system. In any case, as illustrated in FIG. 3, when a frame 40 is to be displayed it is expanded into a matrix 45 consisting of a large number of display points 46 which are determined by an interpolation process from the original frame data points 47. Each point of the matrix is then converted to a visual display point 47 which forms part of the final topographic display 48.

Figure 4:
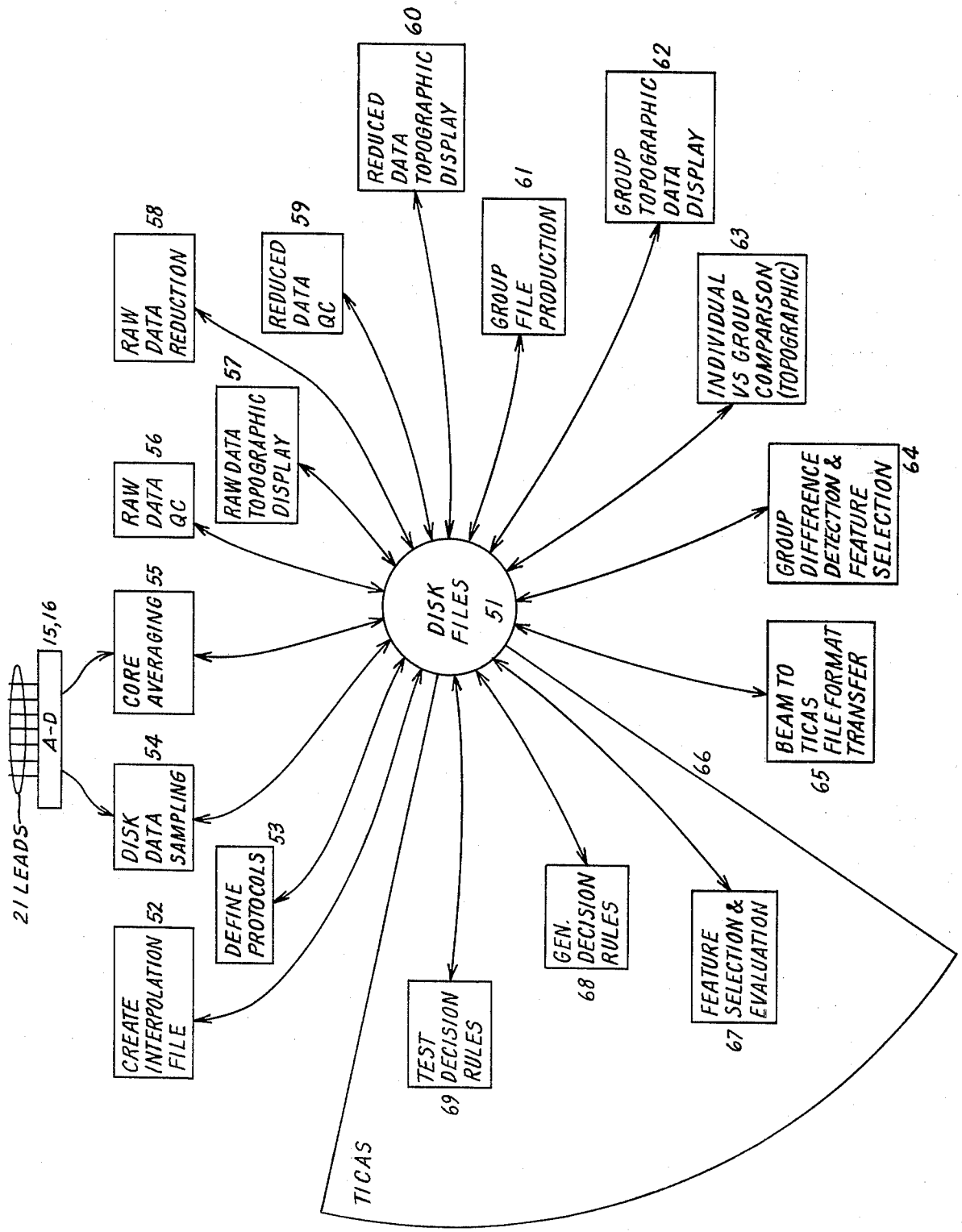
FIG. 4 is a block diagram of the functions performed by the BEAM system.

FIG. 4 illustrates the organization of the operations which comprise brain electrical activity mapping software 28 and TICAS analytic software 29. Raw and processed data is stored in disk files 51. Operations 52-65 and 67-69 use data stored in files 51 to perform data manipulation, data display and data storage functions. Operations 54 and 55 also process data from the outputs of converters 15, 16.

Figure 5:
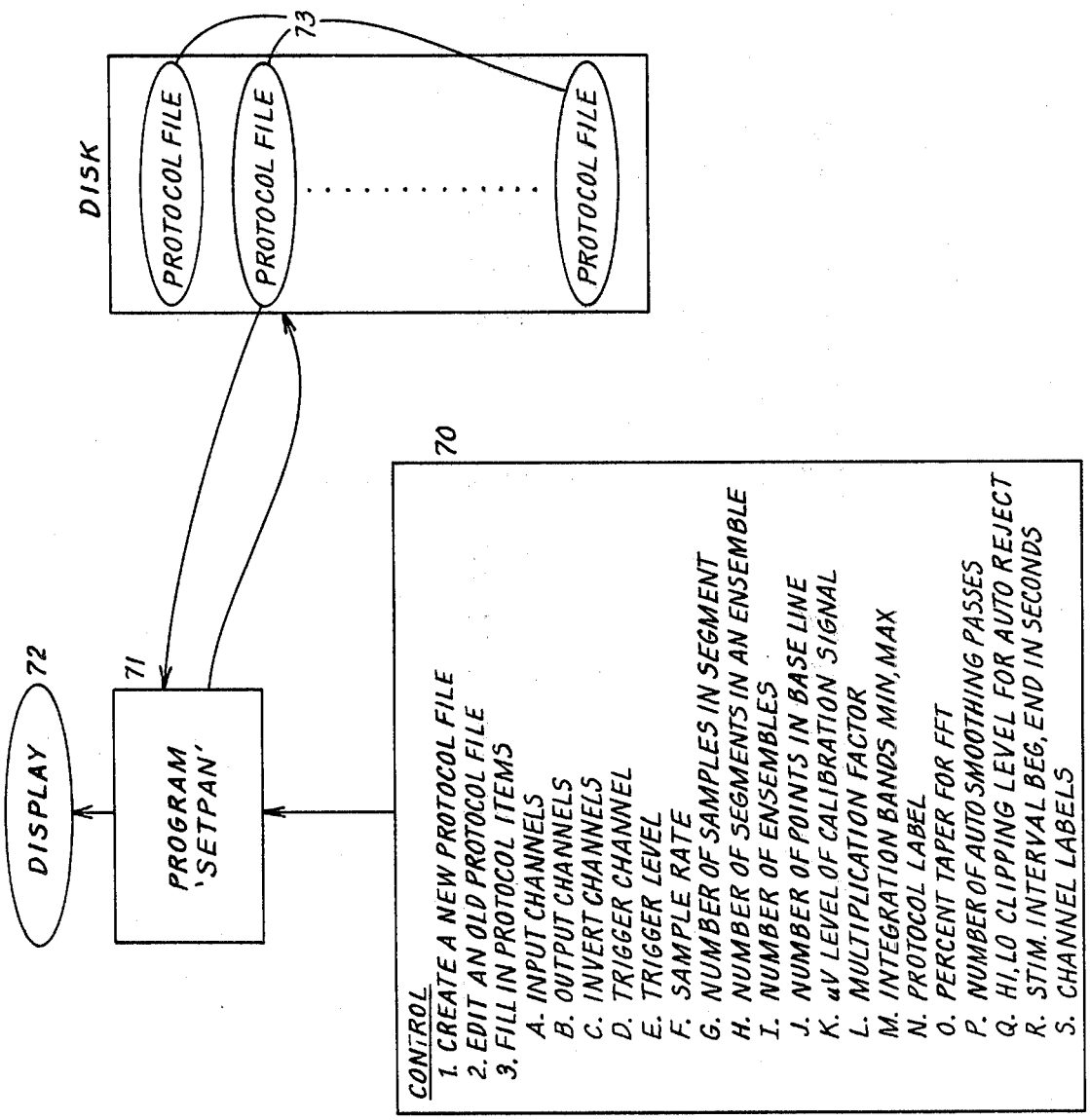
FIG. 5 is a block diagram of the define protocols operation.

FIG. 5 illustrates the function of define protocols operation 53. Protocol files 73 are generated and edited by program 'SETPAR' 71 based on control information 70 provided by the operator through terminal 22, the results of the operation being displayed (block 72) on terminal 22 to the operator. Each protocol file 73 contains information which governs the manner in which other operations are performed on a particular type of data file (e.g., one protocol might apply to the processing of EP transient response data from strobe light stimuli). The protocol information may include the number and identity of input channels, the labeling of the input channels to correspond to specific points on the final display, the identity of the trial marker channel, the voltage level above which to search for the trial markers, the rate in samples per second of sampling of the data, the number of samples in a segment, the number of segments in an ensemble, the number of ensembles, the number of points in a baseline, the microvolt level of the calibration signal (e.g., 100 microvolts at 10 Hz), a multiplication factor, the number (up to 20) and size (width) of integration bands, the label of the protocol, the percent of taper of samples in a segment of data for fast fourier transform processing, the number of automatic smoothing passes, the high and low values for automatic rejection of data during accumulation, the stimulus interval and location in seconds, and channel labels related to electrode positions on the skull.

Figure 6:
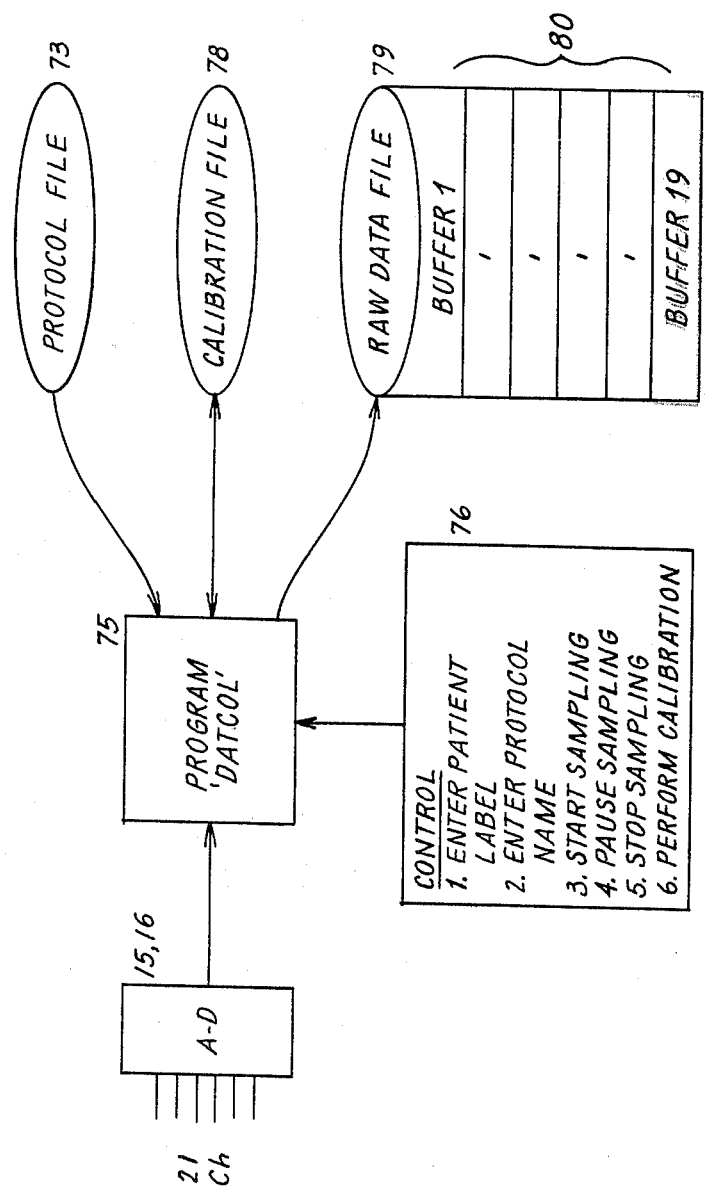
FIG. 6 is a block diagram of the disk data sampling operation.

FIG. 6 illustrates the function of disk data sampling operation 54. Program 'DATCOL' 75 loads raw data from the output of converters 15, 16 into raw data file 79, which is divided into 19 buffers 80 which hold ensembles of data related to particular brain states or stimuli. The operator provides control information 76 designating the patient to whom the data relates and the name of the applicable protocol file 73. Other control information 76 governs the beginning, end, and pauses in data sampling, and the performance of a calibration of signal levels. Calibration data is initially stored in a buffer 80 of raw data file 79. When the operator requests (block 76) a calibration, and designates which buffer 80 contains the raw calibration data, program 'DATCOL' computes the root mean square value and the mean of at least 30,000 points in each channel of calibration data and divides the root mean square value by 0.707 to establish the assumed peak value of the calibration signal. The peak value, representing the level of the original calibration voltage, and the mean value, representing the D.C. offset of the calibration voltage value for each channel, are stored in calibration file 78.

Figure 7:
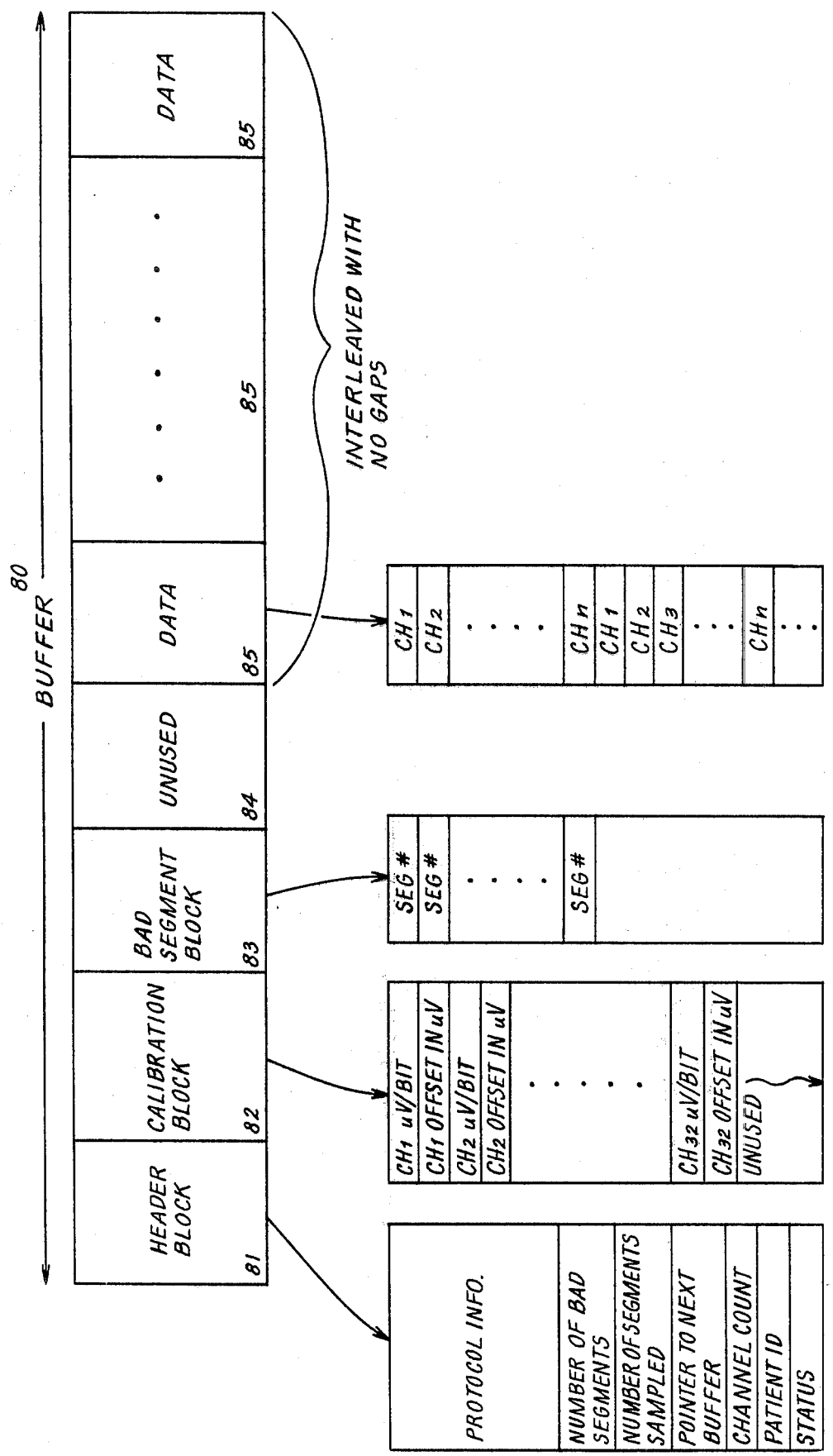
FIG. 7 is a data file format diagram of the raw data file.

The format of raw data as stored in raw data file 79 is illustrated in FIG. 7. Each buffer 80 contains header block 81, having protocol and other housekeeping information concerning the data stored in the buffer; calibration block 82 containing for each channel of data the calibration value in microvolts per bit and the number of microvolts by which the calibration signal was offset from zero both of which values were found in calibration file 78 at the time raw data was loaded; bad segment block 83 identifying segments of data which the operator will later decide to exclude from subsequent operations; an unused segment 84; and a series of data segments 85, which hold a series of data samples, each containing values for all 20 channels. The data segments 85 are interleaved with no gaps.

Figure 8:
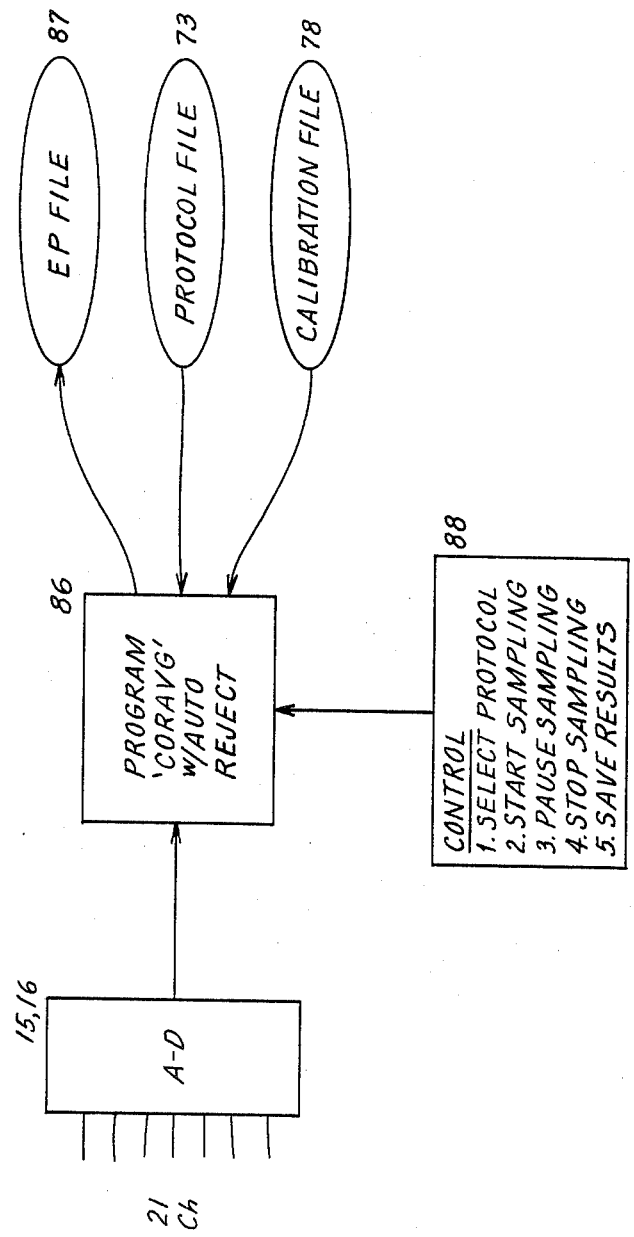
FIG. 8 is a block diagram of the core averaging operation.

FIG. 8 illustrates the function of core averaging operation 55, usually used for loading and signal averaging raw EP transient responses. Data from converters 15, 16 is read by program 'CORAVG' 86. User provided control information 88 designates the protocol, obtained from protocol file 73, under which the operation is performed, and determines start, end, and pauses of the operation. Program 'CORAVG' 86 samples data beginning at points labeled by the prerecorded trial markers and forms signal averaged EP transient responses from a series of transient responses resulting from repetition of a stimulus. The series of transient response data are accumulated and held in EP file 87, which is a reduced data file as described below. Calibration file 78 holds calibration information accumulated from the data channels in the manner previously described. Program 'CORAVG' 86 automatically rejects as "bad data" any segment which contains values outside of preset limits. Program 'CORAVG' 86 also automatically adjusts the zero baseline with respect to each electrode's average EP transient response, by subtracting the mean of the pre-stimulus period values for a channel from each point in that channel's transient response curve.

Figure 9:
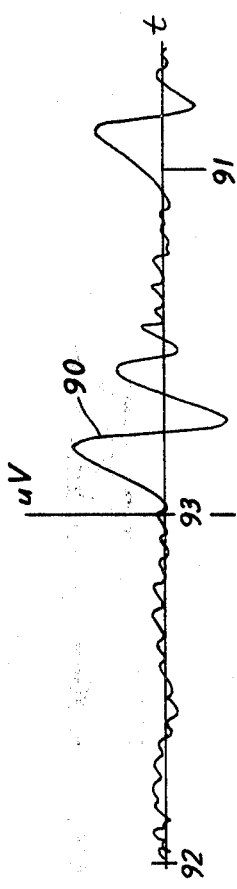
FIG. 9 is a graph of an average EP transient response waveform after automatic baseline zeroing.

FIG. 9 illustrates a plot of an average EP transient response 90 of microvoltage against time as it could be displayed on monitor 18 following core averaging operation 55. The stimulus was presented at time 93, the transient response includes pre-stimulus period between time 92 and time 93, and the plot shows calculated zero baseline 91.

Figure 10:
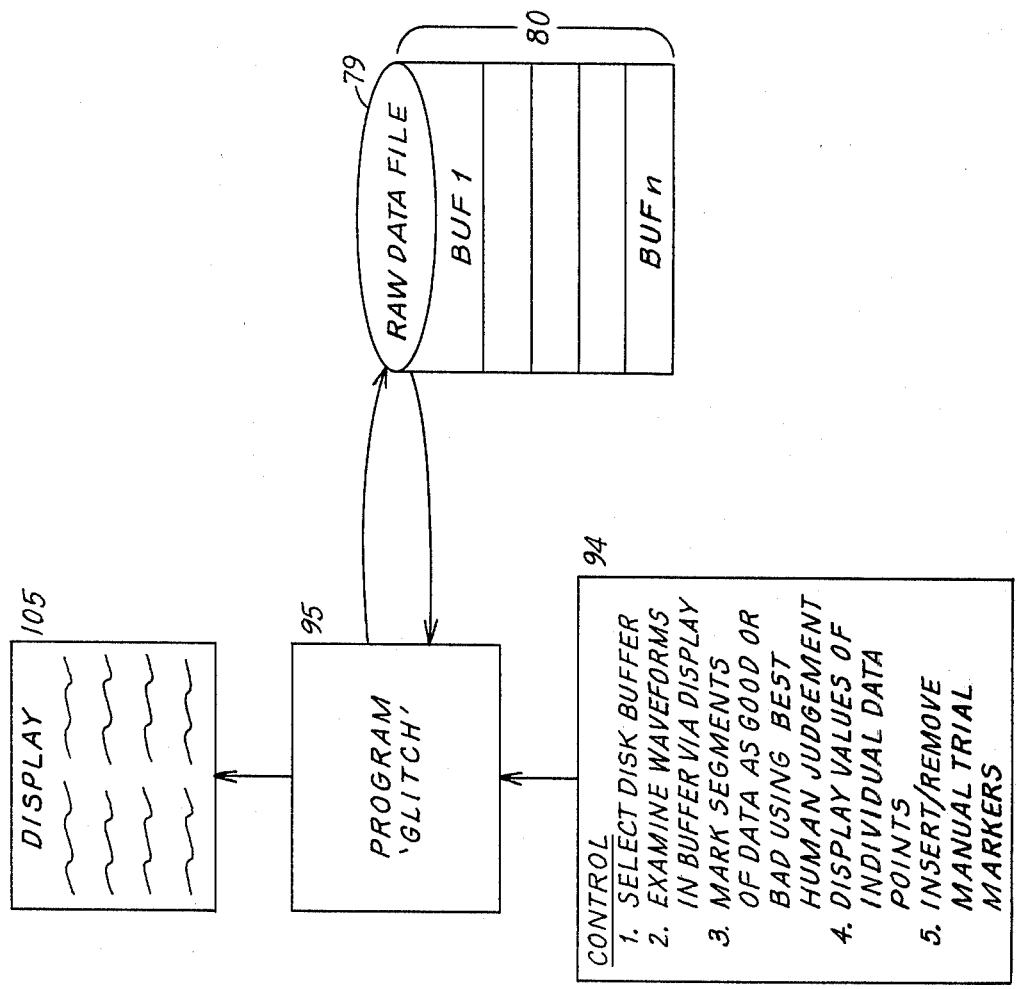
FIG. 10 is a block diagram of the raw data quality control operation.

FIG. 10 illustrates the function of raw data quality control operation 56, which enables the operator interactively to review and eliminate bad segments of raw data before other operations are performed. By means of control information 94 the operator can select for review the contents of any buffer 80 in raw data file 79. The buffer data is displayed (block 105) segment by segment by program 'GLITCH' 95 on television monitor 18 to the operator as an analog waveform. The operator can label any segment of bad data, which causes the bad data segment to be identified on bad segment block 83. Control information 94 can also include the insertion of trial markers indicating a point on a waveform at which subsequent operations should begin, and display to the operator the microvolt value of individual points on a displayed curve.

Figure 11:
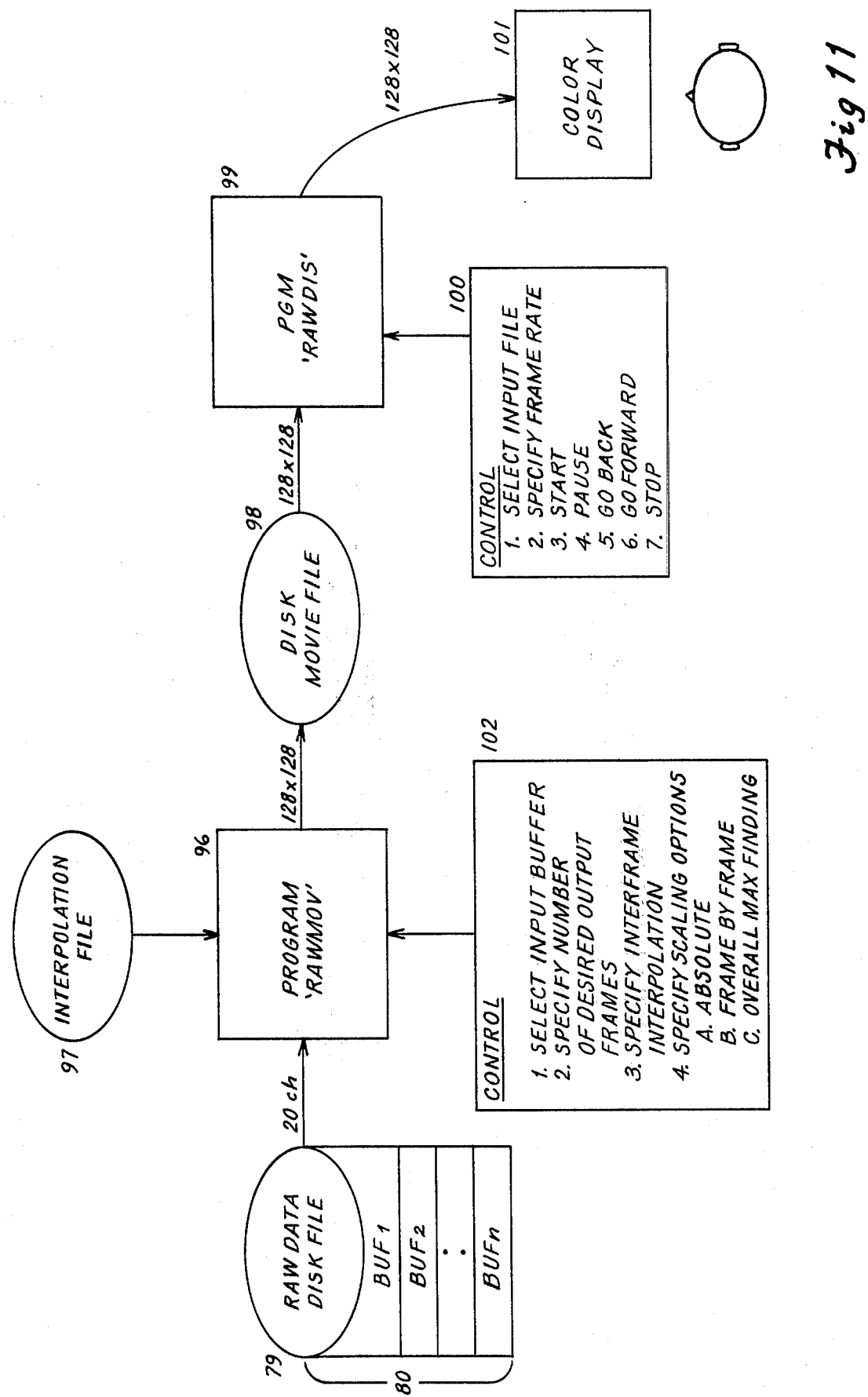
FIG. 11 is a block diagram of the raw data topographic display operation.

FIG. 11 illustrates raw data topographic display operation 57, which provides topographic time sequenced displays (cartoons) of raw data frames. Program 'RAWMOV' 96 expands to 20 channels of each data frame into a matrix of $128 \times 128$ data points by three-point linear interpolation. The operator provides control information 102 designating the disk buffer 80 on raw data file 79 which contains the data to be displayed; the number of display matrices to be produced; the parameters for interframe interpolation; and the parameters and options (described below) for scaling the data points among the available grey color tones of the display. Program 'RAWMOV' 96 calculates each interpolated data point for the display matrix using three-point linear interpolation from the three closest original channels and scales the data to the available grey color tones of the display. The interpolation is performed using preset coefficients stored in interpolation file 97 by an operation described below.

The display matrices produces by program 'RAWMOV' 96 are stored in sequence in disk movie file 98. Program 'RAWDIS' will display (block 101) the frames stored in disk movie file 98 on monitor 20. Control information 100 permits the operator to designate the file to be displayed, the frame rate, and the starting, stopping and reversing of the display sequence. The displays include labels of information taken from the protocol block, e.g., patient identification.

Figure 12:
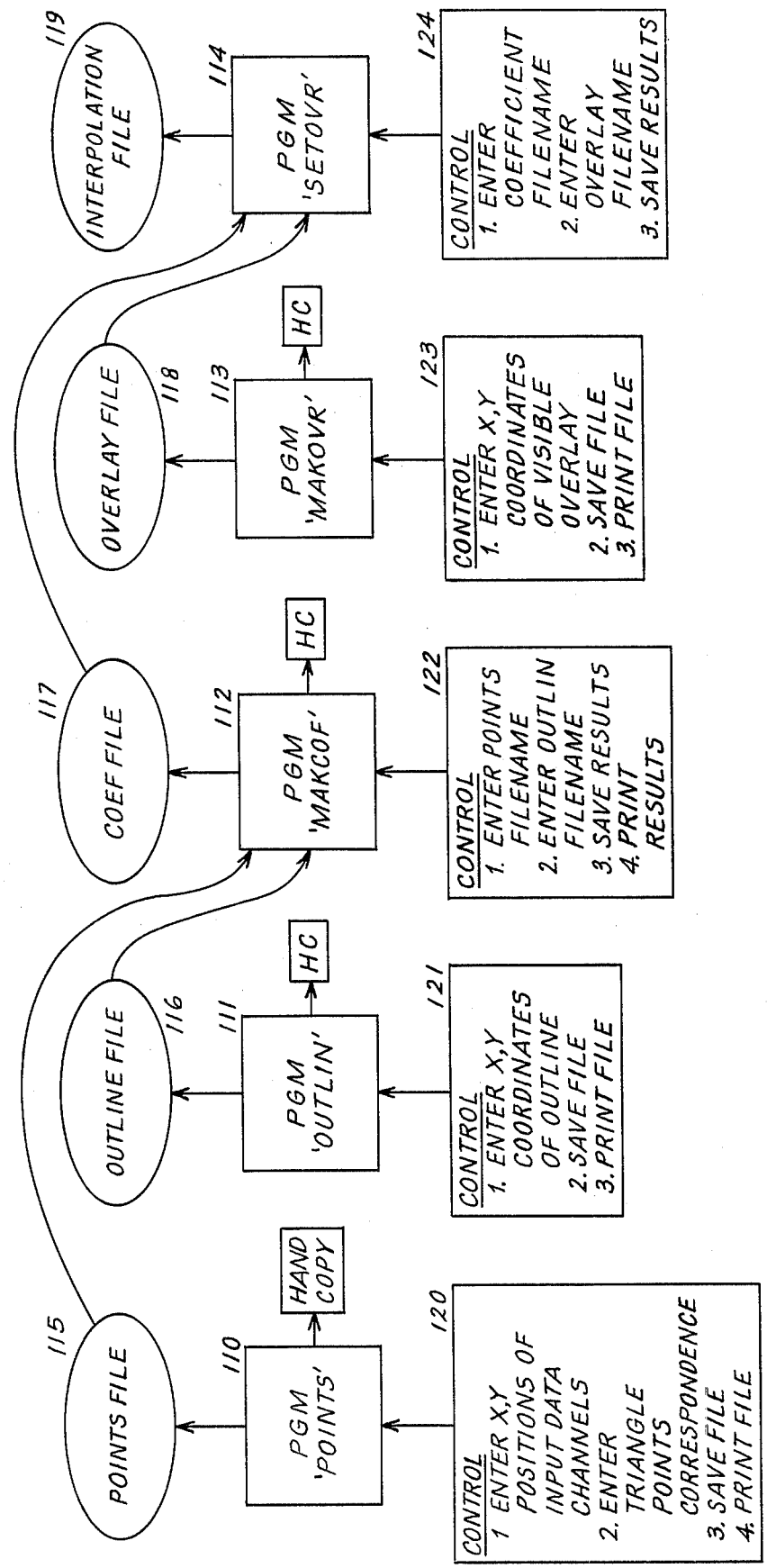
FIG. 12 is a block diagram of the create interpolation file operation.

FIG. 12 illustrates the functions of create interpolation file operation 52. Program 'POINTS' 110 creates points file 115 reflecting the X and Y coordinates of each point in the original electrode layout with respect to the $128 \times 128$ grid and associating with each point in the $128 \times 128$ display matrix the identity of the three original electrode points with respect to which it should be interpolated. Control information 120 provided by the operator includes the X and Y coordinates of each channel and the identity of the three interpolation points for each display point. Program 'OUTLINE' 111 identifies and stores in outline file 116 the X and Y coordinates of the points which outline the plan view of the skull to be included in the display, based on control information 121. Program 'MAKCOF' 112 generates and stores in coefficient file 117 the coefficients needed to perform the three-point liner interpolation for each matrix display point within the skull outline, using points file 115 and outline file 116 as input. Program 'MAKOVR' 113 stores in overlay file 118 the operator provided (block 123) coordinates of the overlay of the skull, nose and ears outline for the display. Program 'SETOVR' 114 generates interpolation file 119 from overlay file 118 and coefficient file 117. Interpolation file 119 then contains the information required to compute interpolated matrix data points and the skull overlay for display.

Figure 13:
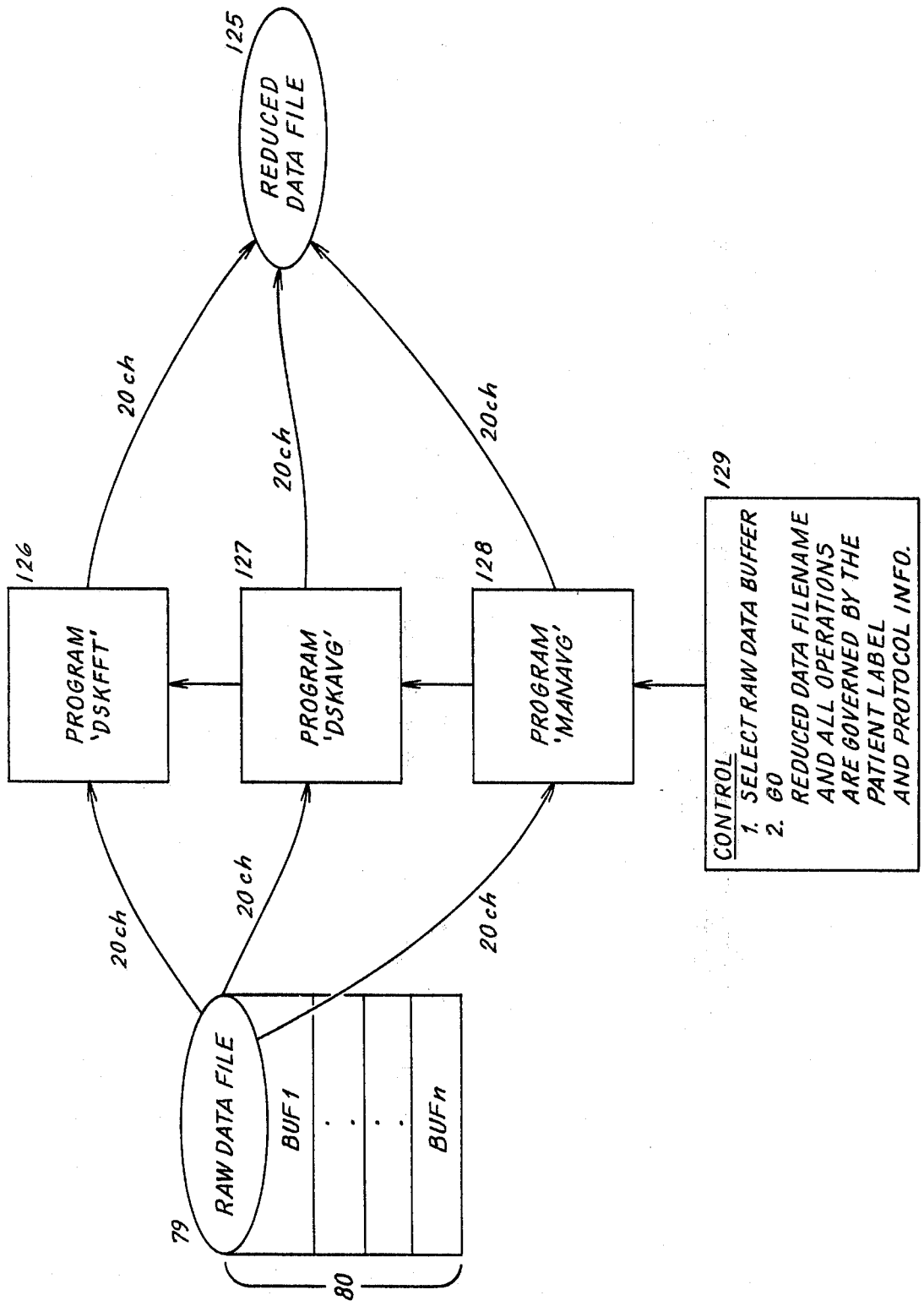
FIG. 13 is a block diagram of the raw data reduction operation.

FIG. 13 illustrates the function of the raw data reduction operation 58. Three alternative programs can operate on data in buffers 80 to produce reduced data files 125. Program 'DSKFFT' 126 accepts segments of EEG data from raw data file 79, performs a fast fourier transform analysis which produces a new segment of data reflecting the spectral energy in each of a sequence of frequency bands. Program 'DSKFFT' 126 also generates, for each group of segments, an ensemble consisting of the sums (used in a later step to form the average values) and sums squared (used in a later step to form the standard deviations) for each channel across all segments in the group, values reflecting each of the sums as a percentage of the total spectral energy in the segment, and values reflecting the coefficient of variation (the standard deviation divided by the mean) for each channel across an ensemble. FIG. 15 illustrates the format of the resulting ensemble of FFT data stored in reduced data file 125. The sums data 130 is filed in sequence by channel for the first frequency band 131, e.g., 0.5 Hz. Similar sums data follows for the other frequency bands. After all sums data is stored, the sums squared data 132, the normalized power spectral density sums, and the coefficient of variation data are stored in similar fashion. In addition to storing the sums and sums squared data for all segments in the ensemble, program 'DSKFFT' can store spectral information for each segment analyzed. As illustrated in FIG. 16, the data is stored as sine and cosine coefficients for each channel for each frequency band, and as normalized sine and cosine coefficients as a percentage of total spectral energy. As illustrated in FIG. 18, the FFT data file 191 stored on reduced data file 125 also includes a header block 192 of housekeeping information.

In FIG. 13, program 'DSKAVG' 127 performs a function similar to core averaging operation 55 in signal averaging EP transient response waveforms, but uses as input raw data stored in raw data file 79 and permits the operator to review each waveform and select those to be used in the averaging process, rejecting others. Program 'MANAVG' 128 permits a similar operator-assisted signal averaging process when the raw data does not contain preset stimulus trial markers, requiring the operator to indicate the point at which averaging is to begin for each waveform. FIG. 14 illustrates the format of signal averaged data produced by programs 'CORAVG' 86, 'DSKAVG' 127 and 'MANAVG' 128. The sums of each channel for all trials for the first time frame 133, e.g., 0-4 milliseconds, are loaded in order, followed by similar information with respect to all subsequent time frames for a given segment. As illustrated in FIG. 17, such EP files 190 are preceded by header block 193.

Figure 19:
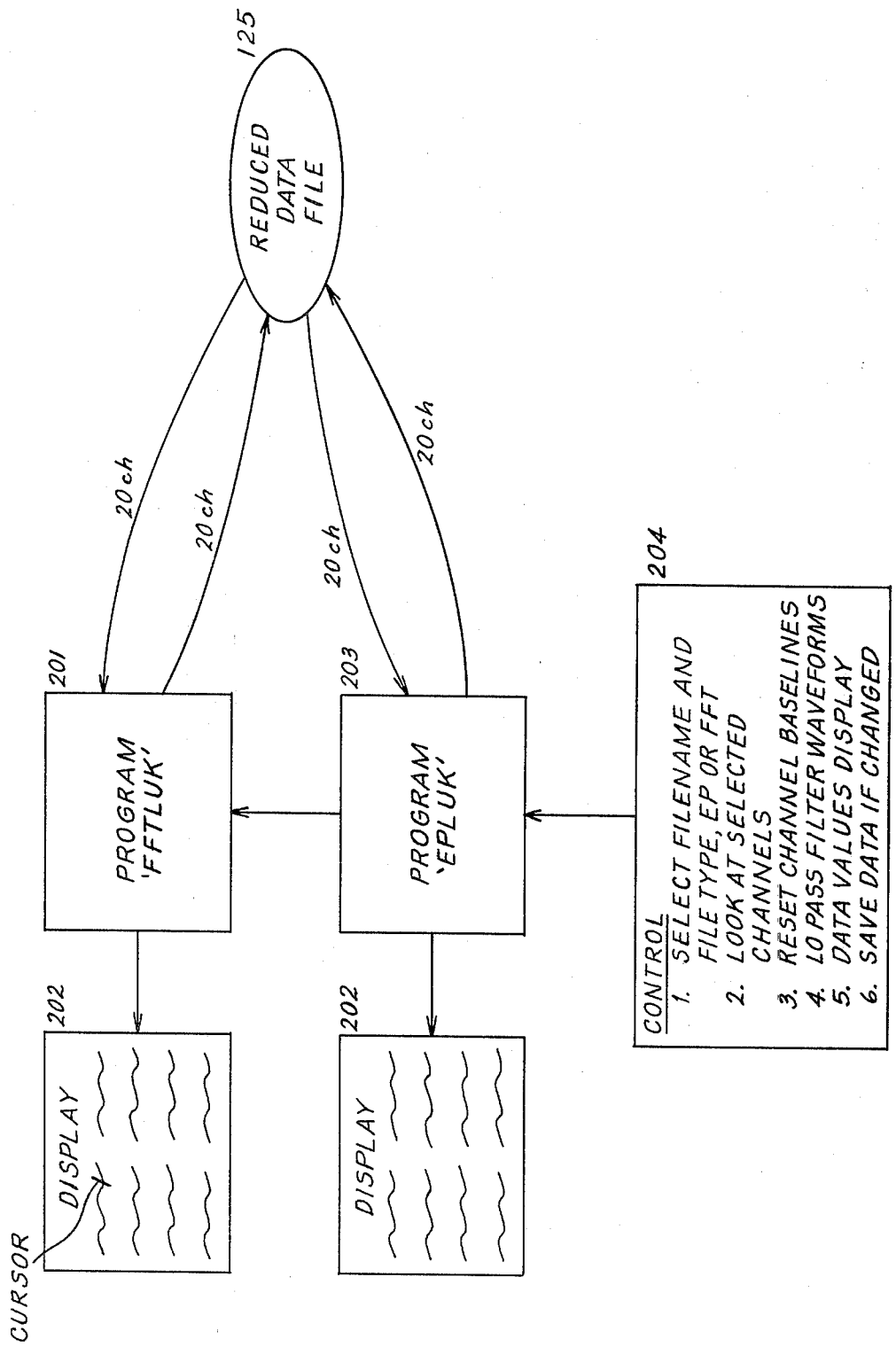
FIG. 19 is a block diagram of the reduced data quality control operation.
Figure 20:
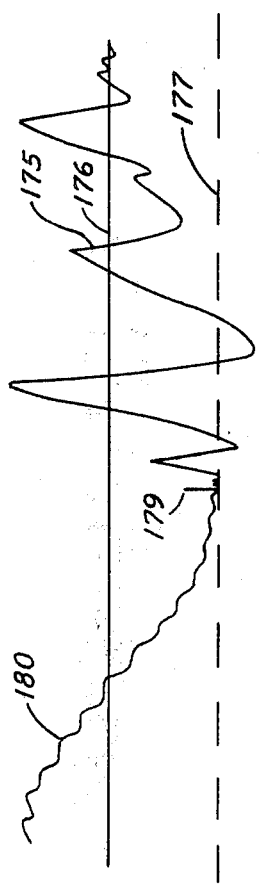
FIG. 20 is a graph of an average EP transient response waveform after automatic baseline zeroing and after manual baseline readjustment.

FIG. 19 illustrates the function of reduced data quality control operation 59, which permits the operator interactively to review and modify data in reduced data file 125. By providing control information 204, the operator can select the file to be reviewed and indicate whether it contains FFT spectral information or EP time-sequenced information. For FFT information, program 'FFTLUK' 201 displays (block 202) selected channels of spectral data as frequency-voltage curves on monitor 18 and permits the operator to low-pass filter the waveforms and display the value of particular data points. For EP data, program 'EPLUK' 203 displays (block 202) selected channels as time-voltage curves and permits the operator to reset the zero baseline, to filter high frequency noise from a channel, and to display the value of any point on a curve. FIG. 20 illustrates the function of manual baseline relocation. Because pre-stimulus period response 180 was not level, automatic baseline 176 set by program 'CORAVG' 86 inaccurately reflects the true zero level for transient response curve 175. The operator can relocate the baseline to a new level 177 by moving cursor 179 to the desired level, causing that voltage value to be subtracted from each point of data along curves 180 and 175.

Figure 21:
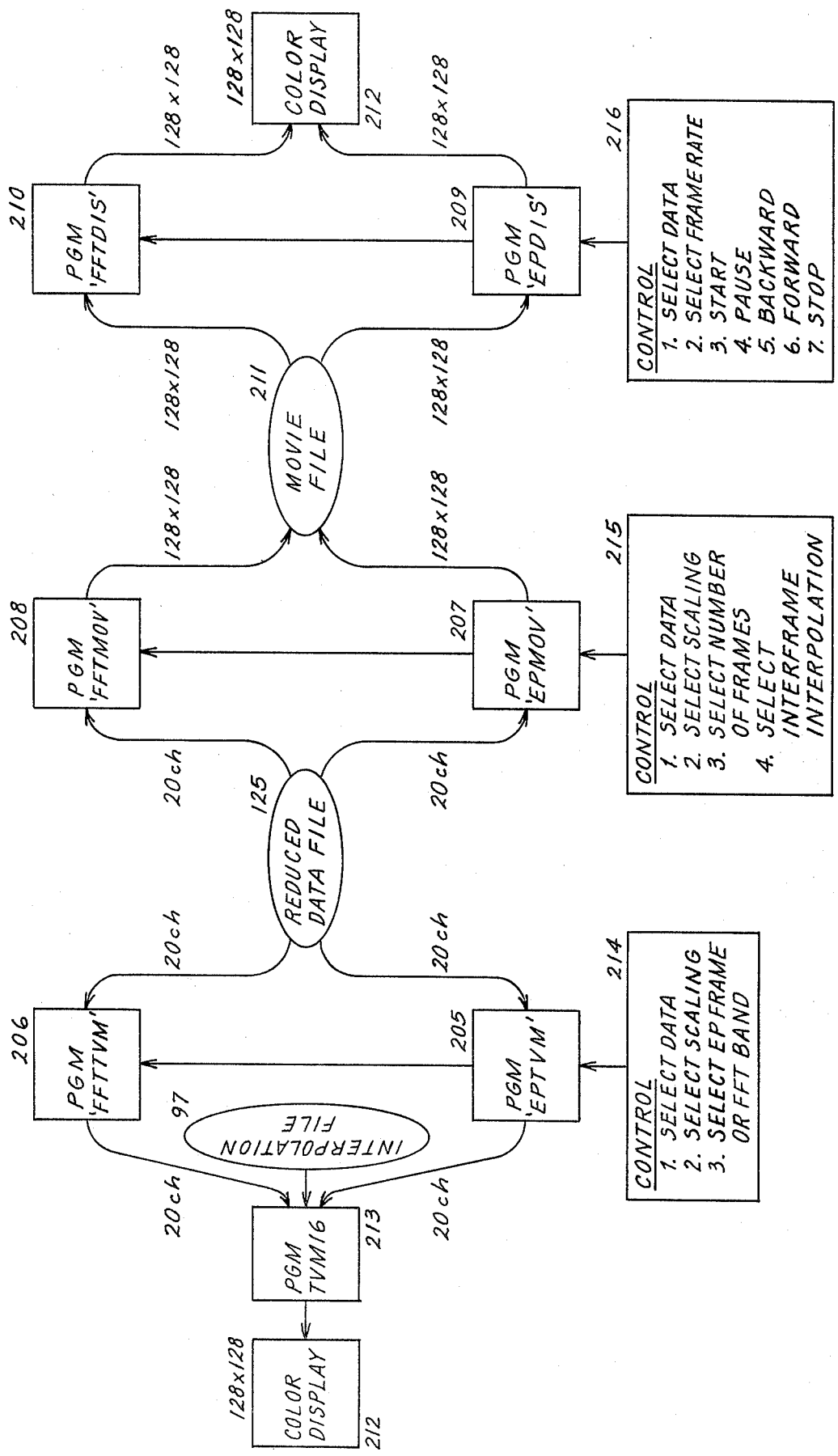
FIG. 21 is a block diagram of the reduced data topographic operation.

FIG. 21 illustrates the functions of reduced data topographic display operation 60. For single frame display of FFT data, program 'FFTTVM' 206 reads data from reduced data file 125 as selected by opeator control information 214. The data is scaled in accordance with instructions included in control information 214. The selected frame is provided to program 'TVM16' 213 which interpolates a matrix of 128×128 points using the coefficients and other information contained in interpolation file 97, and provides the resulting matrix to color display 212. For single frame EP display, program 'EPTVM' 205 performs an analogous process to that of program 'FFTTVM' 206. Programs 'EPTVM' 205 and 'FFTTVM' 206 also perform compilations of sequences of frames into one display matrix, in accordance with predefined groupings set forth in protocol blocks.

A sequence of FFT matrices or EP matrices can be displayed in rapid time sequence as a cartoon by the use of program 'FFTMOV' 208 and program 'EPMOV' 207, respectively, each of which processes sequences of selected matrices of data from reduced data file 125, using scaling control information 215; interpolates full 128×128 matrices for each frame; interpolates a selected number of additional matrices between the original frames; and stores the resulting matrices in movie file 211. Based on control information 216 specifying data to be displayed, the frame rate of display, start, stop, backward, forward and pause, program 'FFTDIS' 210 and program 'EPDIS' 209 provide cartooned matrices for viewing on color display 212.

Figure 22:
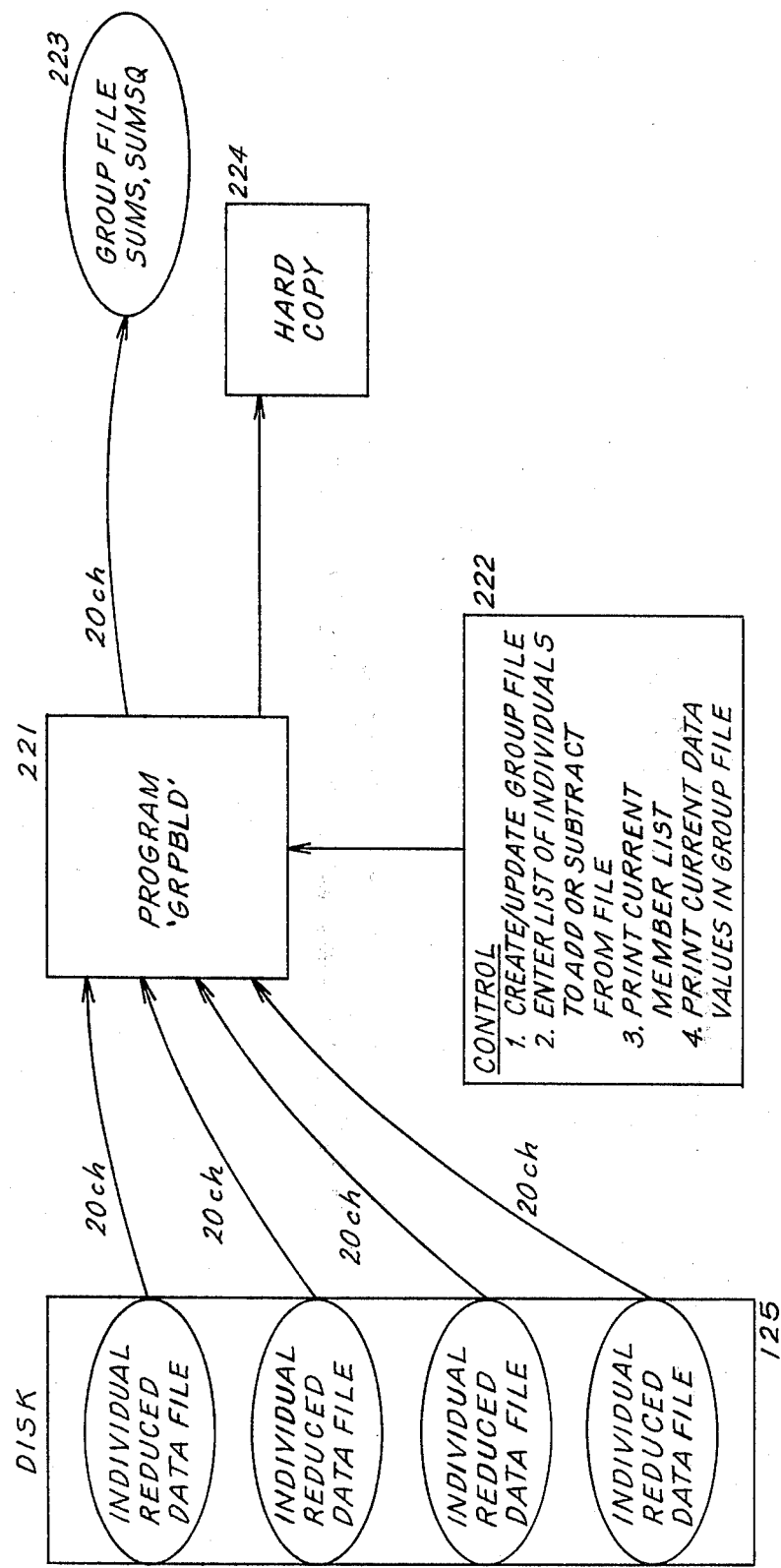
FIG. 22 is a block diagram of the group file production operation.

FIG. 22 illustrates group file production operation 61. Program 'GRPBLD' 221 creates and updates a composite group file 223 working from selected individual reduced data files 125. Control information 222 provided by the operator indicates the identity of individual reduced data files to be included. The group files 223 consist of the sums and the sums squared for all homologous points in the reduced data files 125 of all individuals in the group. Normalized sums and coefficients of variation may also be produced and stored. Hard copy 224 listing the individuals in each group and the values of group file data are available based on control information 222.

Figure 23:
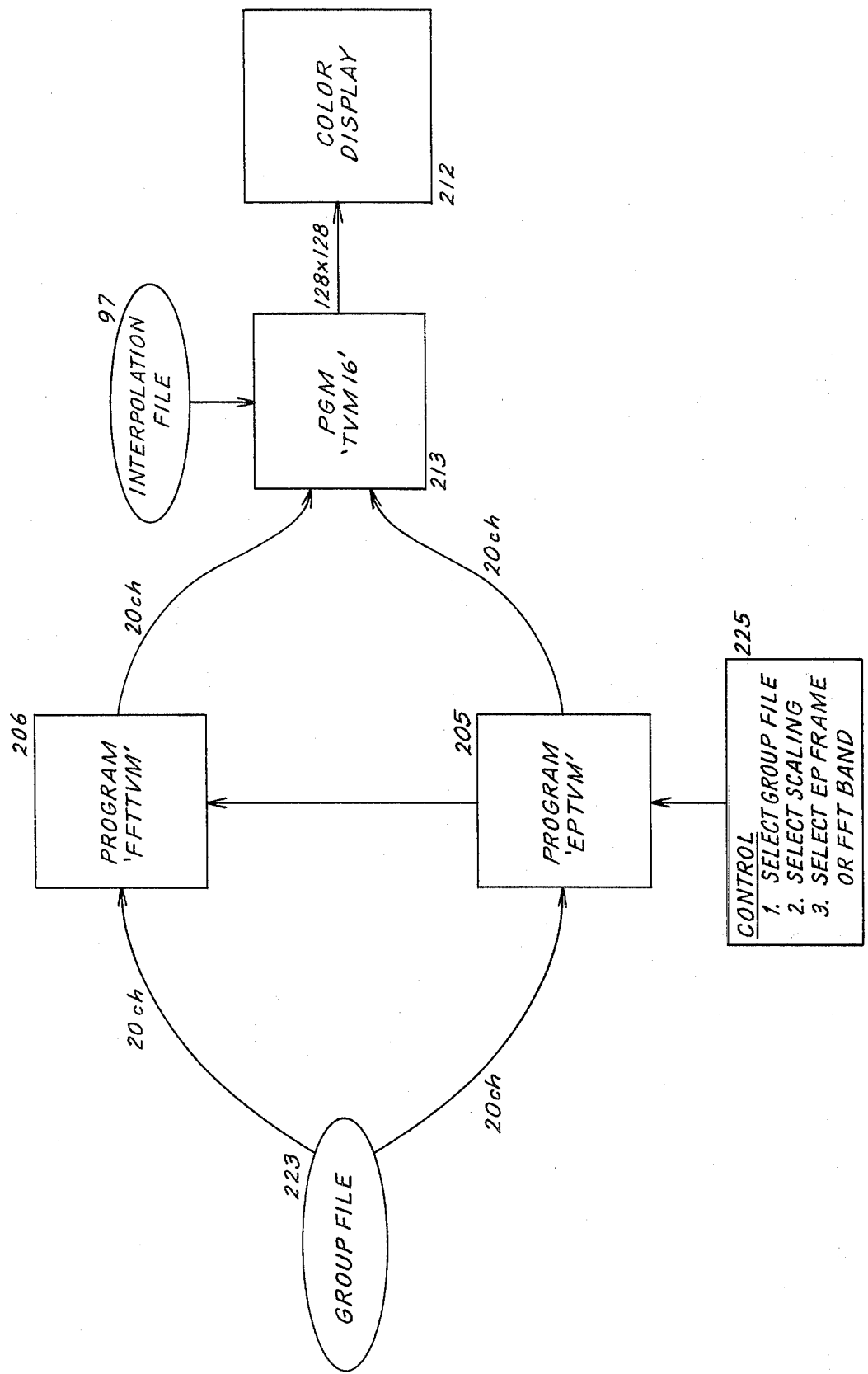
FIG. 23 is a block diagram of the group topographic display operation.

FIG. 23 illustrates the function of group topographic data display operation 62 which is analogous to the operation of the single frame display of reduced data file information, illustrated in FIG. 21, except that the data displayed is from group file 223 instead of reduced data file 125.

Figure 24:
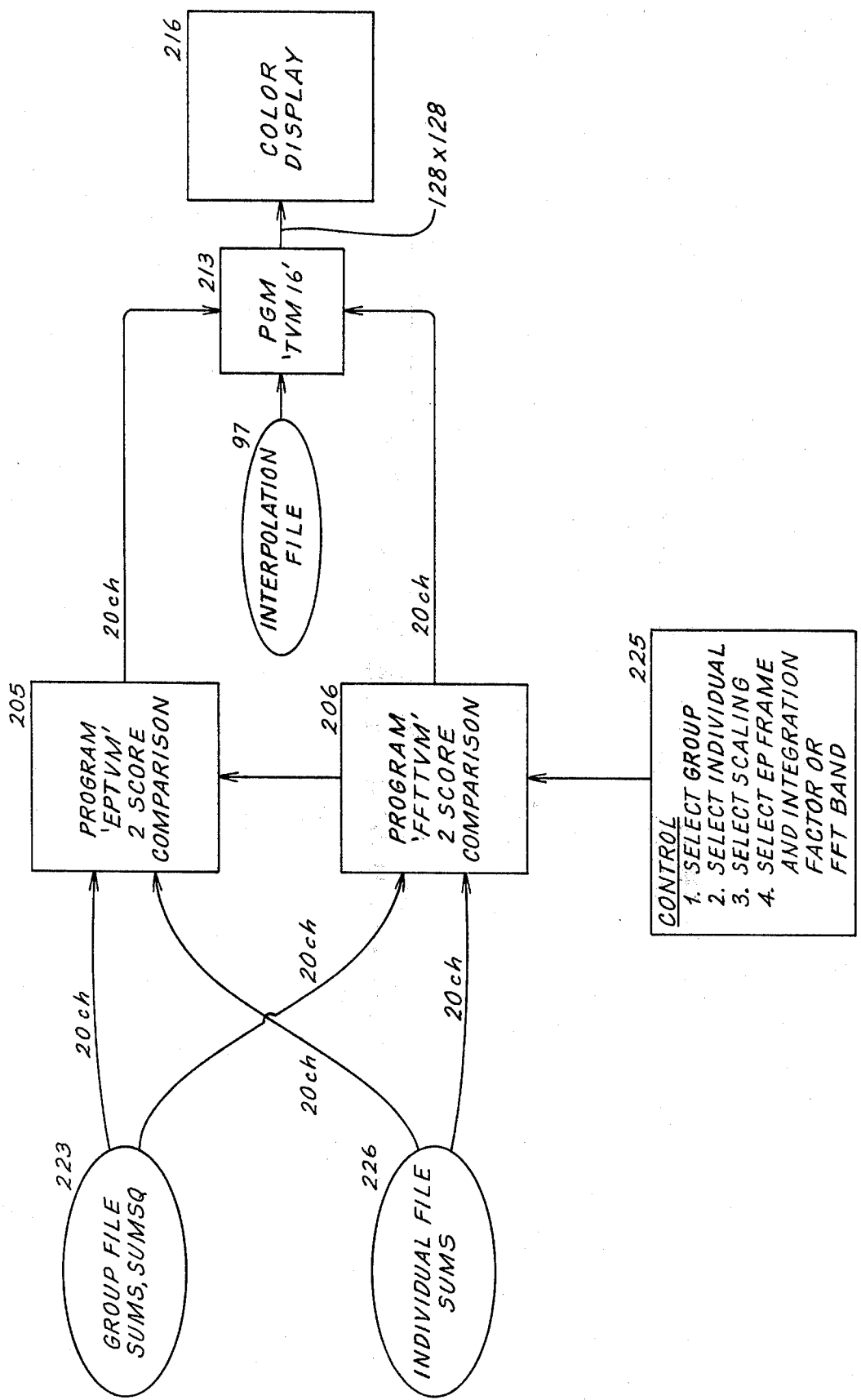
FIG. 24 is a block diagram of the individual vs. group comparison operation.

FIG. 24 illustrates the function of individual versus group comparison operation 63. Programs 'EPTVM' 205 and 'FFTTVM' 206 are performed respectively on EP and FTT data. In each case, the program generates a frame of points, each of which is the number of standard deviations (z-statistics) by which an individual's point, taken from individual file 226 differs from the average of the group's corresponding points taken from group file 223. The resulting frame is displayed (block 216) by program 'TVM16' 213, which interpolates additional data points to form a $128 \times 128$ matrix in the manner previously described.

Figure 25:
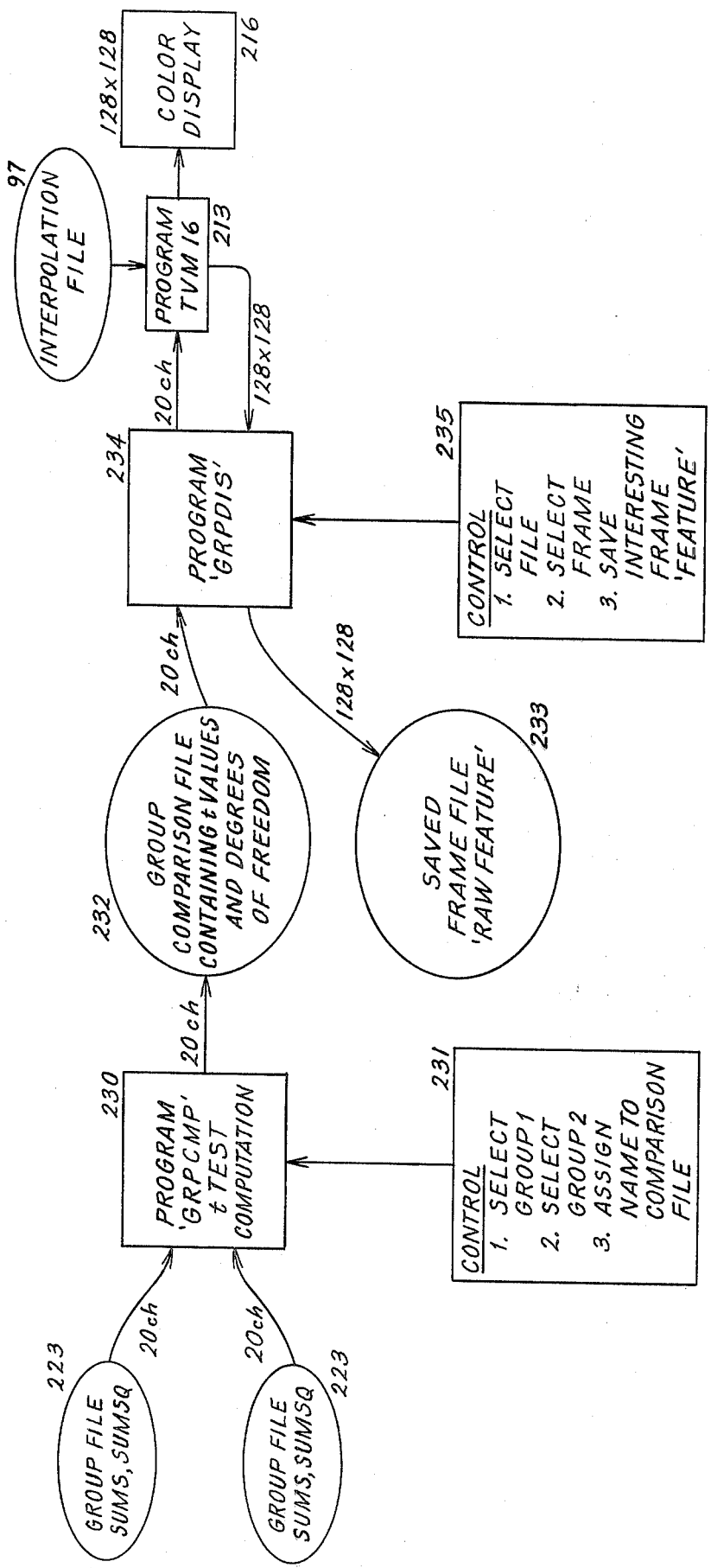
FIG. 25 is a block diagram of the group difference detection and feature selection operation.
Figure 26:
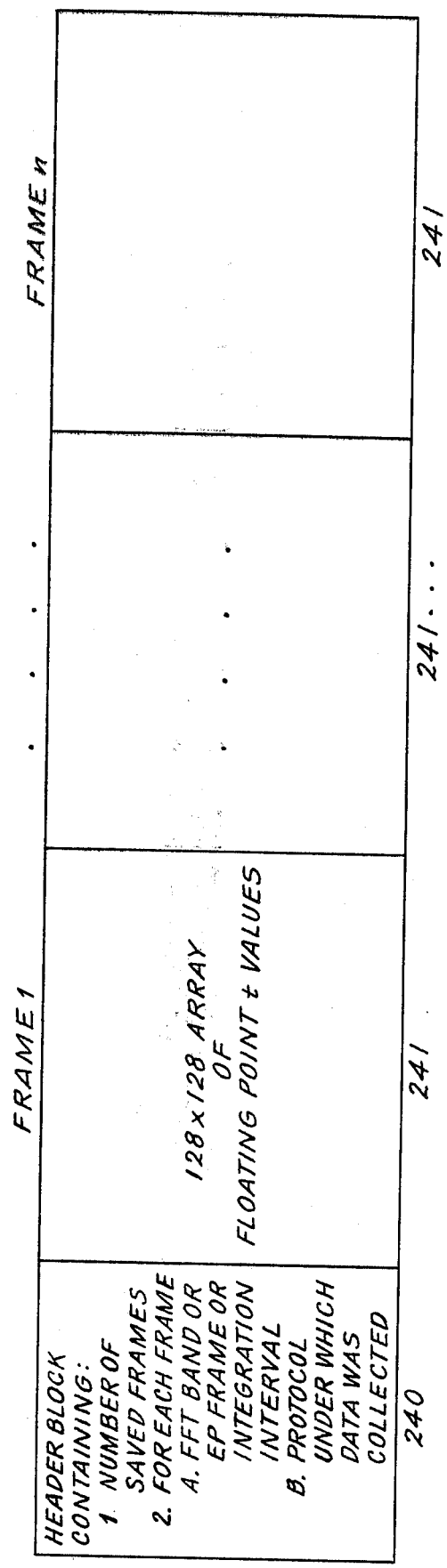
FIG. 26 is a data file format diagram of a saved frame file.

FIG. 25 illustrates the function of group difference detection and feature selection operation 64, which computes frames of t-statistics reflecting the level of statistical difference between two groups based on the means and standard deviations of homologous data points for the two groups. Program 'GRPCMP' 230 computes t-statistics and degrees of freedom from the sums and sums squared data contained in two different group files 223 designated in control information 231 provided by the operator. The resulting frames are stored in group comparison file 232. Based on file and frame designations set forth by the operator in control information 235, program 'GRPDIS' 234 transmits a selected t-statistic frame for display by program 'TVM16' 213 as previously described. Program 'TVM16' 213 also returns a fully expanded $128 \times 128$ matrix back to program 'GRPDIS' 234. Through control information 235, the operator may store such a t-statistic matrix in saved frame file 233. FIG. 26 illustrates the format of saved frame file 233. Header block 240 contains the number of saved frames, and for each frame identifies the time frame length or frequency band and the protocol under which the data was collected. Frames 241 contain $128 \times 128$ matrices of floating point t-statistics generated by program 'GRPDIS' 234.

Figure 27:
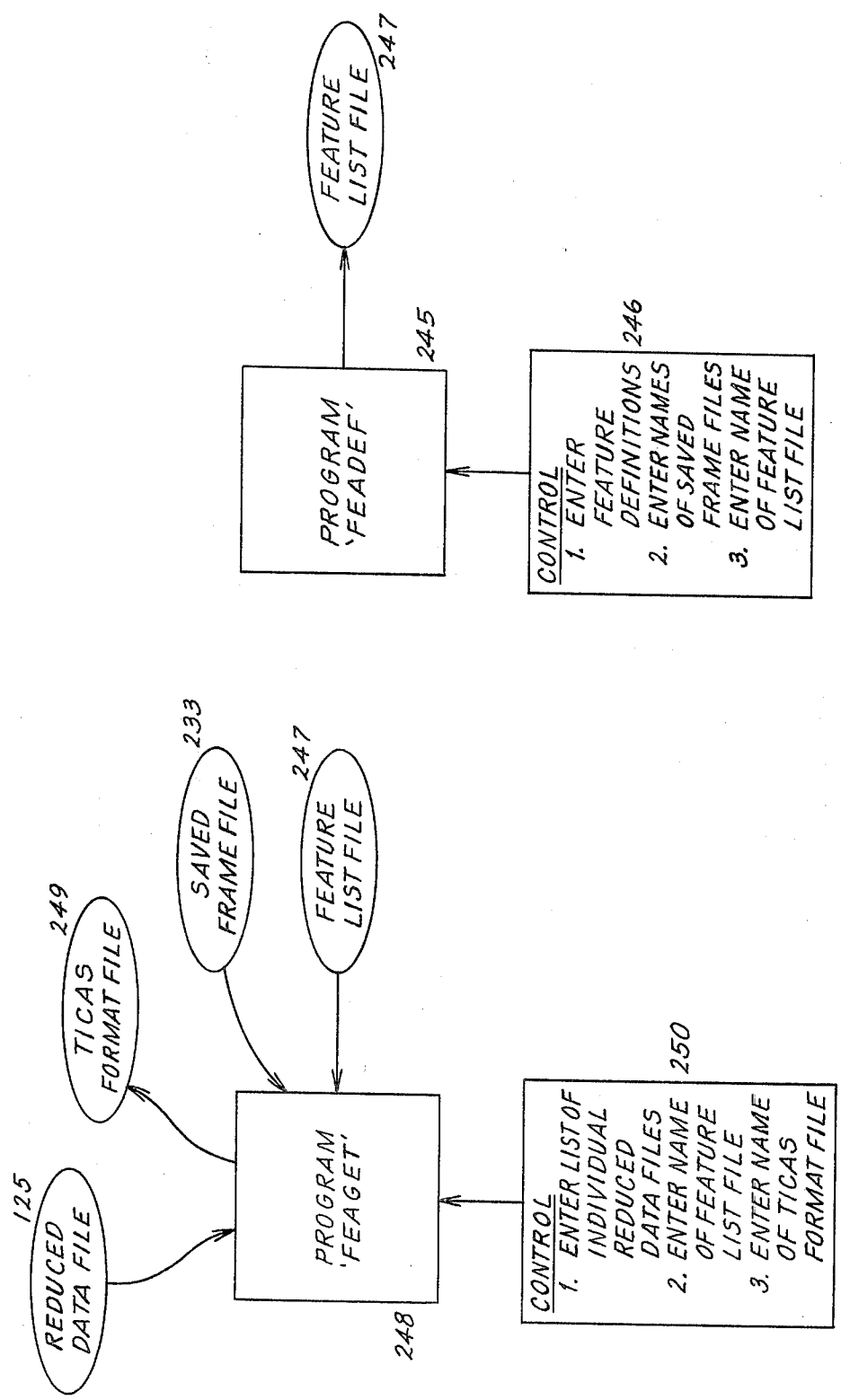
FIG. 27 is a block diagram of the brain electrical activity mapping to TICAS file transfer operation.

FIG. 27 illustrates the functions of the brain electrical activity mapping to TICAS file transfer operation 65, which converts features of brain electrical activity mapping data to a form usable with TICAS software 29. Program 'FEADEF' 245 generates features list file 247 from feature definitions and names of saved frame files 234 provided by the operator in control information 246. Program 'FEAGET' 248 then generates TICAS format file 249 from reduced data files 125, saved frame file 233, and feature list file 247, identified by the operator in control information 250. The feature definitions which may be selected and stored in TICAS format file 249 for subsequent TICAS analysis include nearly all combinations of data found in all individual files, all combinations of integrated bands of frames (e.g., alpha bands) in individual files grouped according to preset protocol specifications, or combinations of individual frame files weighted by the values in a saved t-statistic frame.

Figure 28:
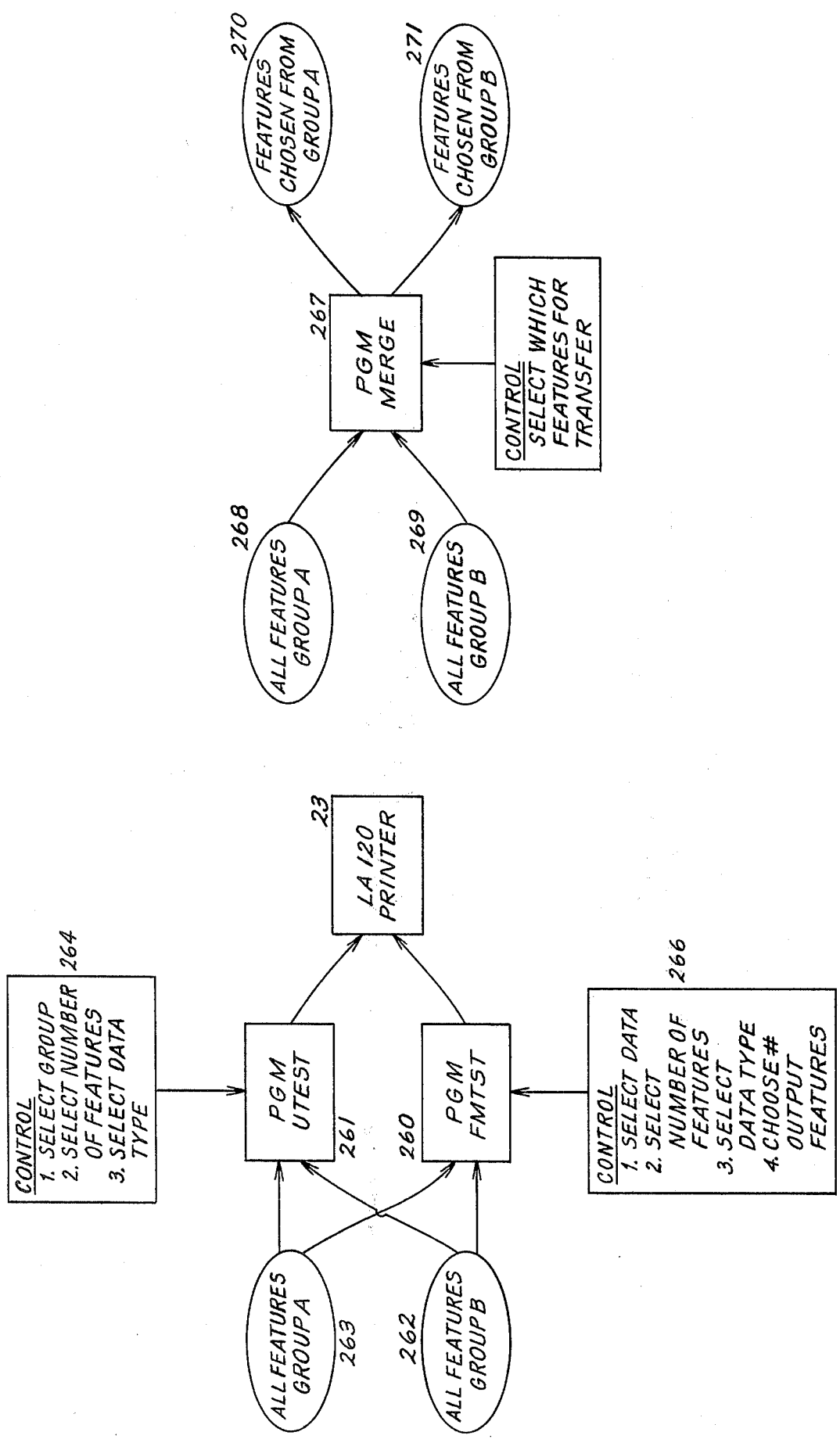
FIG. 28 is a block diagram of the TICAS feature selection and elevation operation.

FIG. 28 illustrates the functions of TICAS feature selection and evaluation operation 67. In control information 266, 264 the operator designates two groups 262, 263 from TICAS format file 249 whose features are to be analyzed, the type of data to be analyzed, the number of input features to be analyzed, and the number of output features to be produced. Program 'UTEST' 261 performs a standard two-sample Wilcox-Mann-Whitney U-test and provides a list of U-test scores in rank order which are printed on printer 23 and stored. Program 'FMTST' 260 performs a final merit value (FMV) test and provides and stores a list of values for features in order of final merit values. Program 'FMTST' 260 first determines intermediate merit values as a combination of the standard receiver operating characteristic (ROC) curve or d' value and the results of an ambiguity function analysis. The final merit values for each feature are then determined by correlation of the intermediate merit value with all features ranked higher in intermediate value. Program 'MERGE' 267 selects from Group A features 268 and Group B features 269, based on the FMV values and U values, those features which are most useful, which are then stored in disk files 270 and 271.

Figure 29:
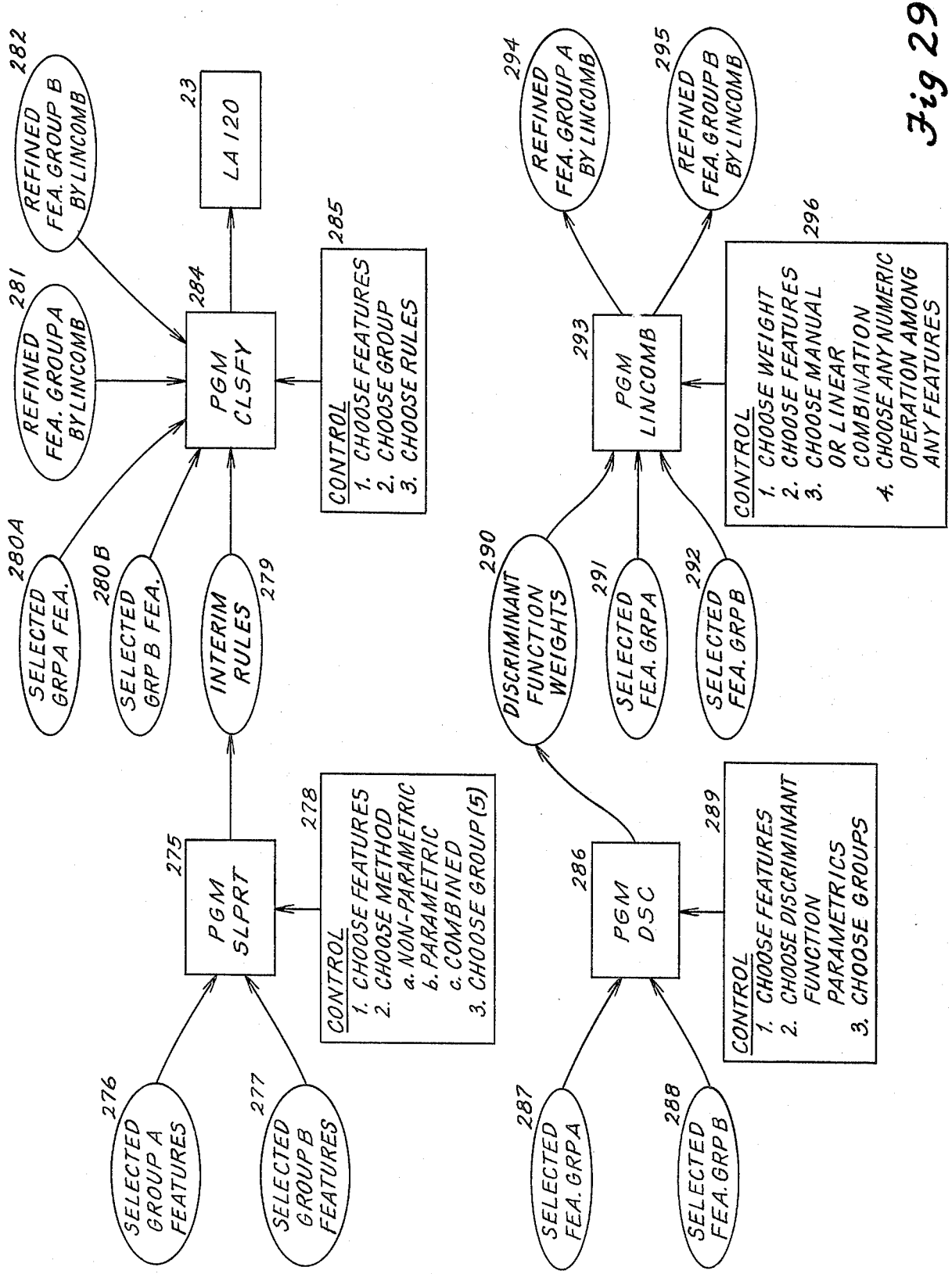
FIG. 29 is a block diagram of TICAS generate decision rules operation.

FIG. 29 illustrates the functions of TICAS generate decision rules operation 68. Program 'SLPRT' 275 uses an operator controlled (block 278) subset of selected Group A features 276 and selected Group B features 277 to generate disk stored interim rules 279, by a method controlled (block 278) by the operator. The computation method may be a non-parametric d-selection technique, a parametric classification technique, or a combination of the two. Program 'CLSFY' 284 uses operator selected (block 285) interim rules 279 to classify operator selected subjects having operator selected features, from selected group features files 280 or refined group features files 281, 282, printing the results on printer 23, thereby permitting the operator to evaluate the efficacy of each selected interim rule 279. Program 'DSC' 286 combines operator chosen (289) features from selected Group A features 287 and selected Group B features 288 into new features on the basis of the weighting functions of a standard linear discriminate analysis, subject to the operator's choice (group 289) of discriminant function parameters. Discriminant function weights for the best features are then loaded into a disk file 290. Program 'LINCOM B' 293 uses the original selected Group A features 291 and selected Group B features 292 and the discriminate function weights 290 to create refined Group A features 294 and refined Group B features 295, which are linear or other operator selected (block 296) combinations of the original features. Refined Group A features 294 and refined Group B features 295 can replace the original selected features 276 and 277 as input to program 'SLPRT' 275 to permit an iterative process of decision rule generation.

Figure 30:
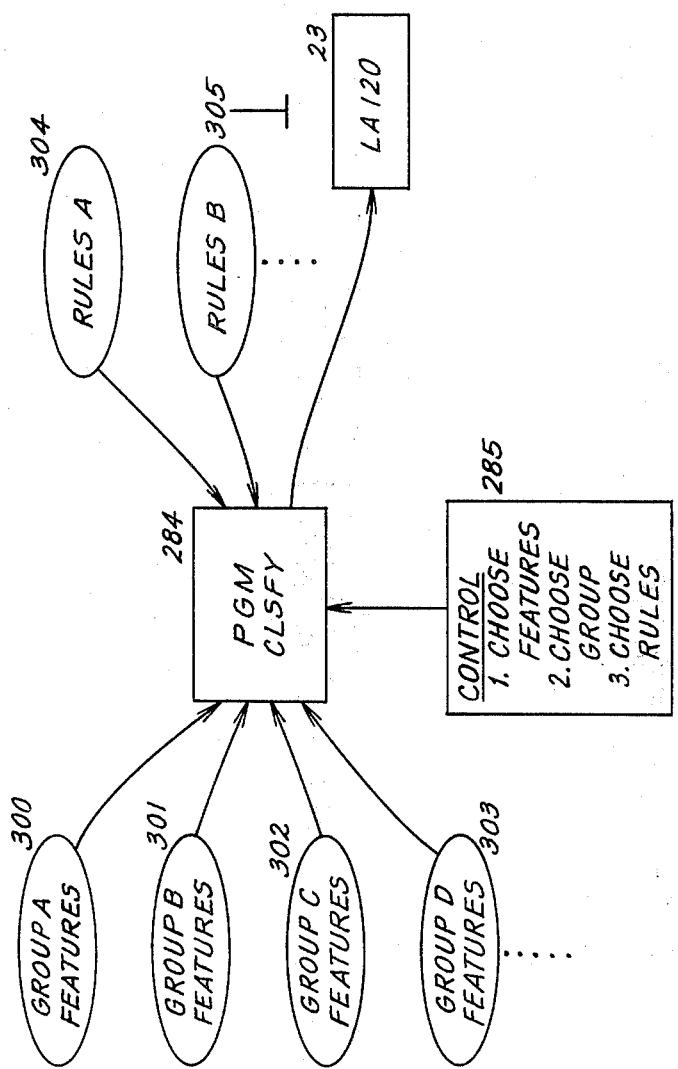
FIG. 30 is a block diagram of TICAS test decision rules operation.

FIG. 30 illustrates test decision rules operation 69. Program 'CLSFY' 284 uses final sets of decision rules, e.g., rules A 304 and rules B 305, to classify individuals in original Group A 300, original Group B 301 and new unknown groups, e.g., Group C 302 and Group D 303, to determine the efficacy of the final decision rules, the results being provided on printer 23.

OPERATION

DATA GATHERING

Accumulation of raw EEG and EP data is accomplished by first attaching 20 electrodes 5 to the scalp of an individual subject in a conventional international 10-20 format. In other embodiments, information from between 10 and 200 electrodes can be gathered and analyzed. Before recording, and if desired during recording, the operator observes the signal levels on the 20 channels of chart recording of polygraph 10 and adjusts the gain on weak signals to produce usable waveforms. A calibration signal of 100 microvolts (10 Hz) from source 8 is recorded on all twenty channels on tape recorder 11 at the beginning of each session and whenever any of the gain levels on polygraph 10 is adjusted.

Data gathering typically begins with a careful administration of a sequence of tests, each of which is intended to establish a particular steady-state electrical condition in the subject's brain. The sequence of tests usually includes instructions to relax and remain still with eyes open, to relax and remain still with eyes closed, to become drowsy, to breathe deeply for hyperventilation, to listen to music and to listen to speech. Other tests require the subject to (1) listen carefully to a story and answer simple questions about its content when completed, (2) remember a set of six abstract figures (often resembling an unknown language alphabet) in black ink on index cards presented by the examiner, (Kimura Figures-Instruction) (3) select the six previously presented figures from a set of 36 figures, verbally indicating yes or no (Kimura Figures-Test), (4) associate each of four abstract figures on index cards with a particular artificial name spoken by the examiner (Paired Associates-Instruction), (5) name each of the four abstract figures when tested by the examiner (Paired Associates-Test), (6) read silently three previously unread paragraphs (e.g., example text from the Gray Oral Reading Test) so as to anser questions subsequently (Reading Test-Instruction), (7) identify whether 34 typed sentences presented by the examiner were previously included in the three paragraphs (Reading Test-Test), and (8) read text upside down: The tests are designed to permit recording of brain electrical signals during simple resting brain activity and during different levels of activation of the left hemisphere, the right hemisphere and both hemispheres of the brain together. This permits the demonstration of pathologies present at rest and those present upon brain activation. The development of specific tests and the choice of tests is determined by the user based in part on the subject being tested and the information being sought as described in greater detail below. Between twenty seconds and three minutes of steady state brain electrical activity is recorded on all 20 channels during each of the tests. Appropriate records of the tape location of each test are kept. These tests have been used with the brain electrical activity mapping system to demonstrate group differences between normal subjects and those with dyslexia or specific reading disability at the 10–12 year age level and at the six-year age level; to differentiate demented patients from normals and aged patients from younger patients in clinical settings; to identify patients with an organic basis for sociopathic behavior and other forms of mental illness; to demonstrate epilepsy when the resting background EEG failed to show any abnormalities; to demonstrate abnormalities in EEG and EP data for schizophrenic subjects; and to determine when a brain tumor, previously treated, is about to recur.

With young infants, the brain states tested include sleep, alert and attending to visual and auditory stimuli, alert but not attending to visual and auditory information, and drowsiness. Using these states, it is possible to discriminate among children with poor behavioral scores on a psychological test and those with high psychological scores.

A series of sensory evoked potential (EP) transient responses are then recorded from all electrodes while the subject is repeatedly exposed to a selected stimulus, e.g., a strobe light or a click generator or to a predetermined sequence of two alternate stimuli. Because the EP transient response is weak compared to the background steady-state brain electrical activity, the stimulus must be presented many times (e.g., 500) to the subject for later signal averaging. The total response period of interest is typically 1024 milliseconds, comprising 512 milliseconds before stimulus and 512 milliseconds after stimulus. The process is repeated for different stimuli.

Stimuli presented to the subject can range from simple falsh, simple click, simple pattern reversal and simple somatosensory stimulation to those requiring complex decisions. Requiring a subject to discriminate between subtly different auditory stimuli (e.g., the words "tight" and "tyke") is useful in diagnosing dyslexia. This procedure is known as the Tight-Tyke evoked potential phenomic discrimination test. Picking an infrequently different stimulus from among other more frequent stimuli is useful evaluating subjects who have functional brain disorder.

Auditory stimuli generate a set of fast and a set of slow transient responses. The fast responses eminate from the brainstem and have a typical duration of 20 milliseconds. Brainstem responses are normally sampled for a total response period of 40 milliseconds comprising 20 milliseconds before stimulus and 20 milliseconds after stimulus. Filters 12 are adjusted to exclude frequencies below 300 Hz and to include frequencies up to 8000 Hz.

When EP transient responses from such stimuli are averaged to eliminate noise, two types of interference can occur. The first type, known as contingent negative variation (CNV), relates to the connection made by the brain between consecutive equally spaced stimuli when the subject is told to count the stimuli. The D.C. component of the resulting transient response shows a gentle dip and a sharp rise immediately before each stimulus, attributable to the subject's anticipation of the next stimulus. The sharp rise contaminates the evoked potential transient response and makes it difficult to establish a zero baseline. By including as part of the interval between stimuli a first pseudorandom time element which varies from 0 to a period longer than the post-stimulus response and is also a multiple of the wavelength of the interfering frequency described below, the CNV effect is greatly reduced.

The second type of interference results from the existence of background noise at certain characteristic frequencies, e.g., 10 Hz, which reflect prominent bands of steady-state brain wave activity. The major interfering frequency of a given subject may be determined by a spectral analysis of his background EEG signal. The interference problem is especially significant in adults with prominent alpha waves and children with prominent slow brain wave activity. By including in the time interval between stimuli a second pseudorandom time element whose period varies from zero to the wavelength of the major interfering frequency, the background noise can be substantially reduced in the averaging process.

The inclusion of a prestimulus period of recording for each transient response permits an accurate baseline determination at a later stage of signal processing in order to establish a true zero level for the post-stimulus response and permits a determination of the quality of the signal averaging process.

Pseudorandom stimulus controller 9 measures the interval between stimuli as a combination of the post-stimulus response period, the first pseudorandom perdio described above, the second pseudorandom period described above, and the pre-stimulus response period.

Figure 31:
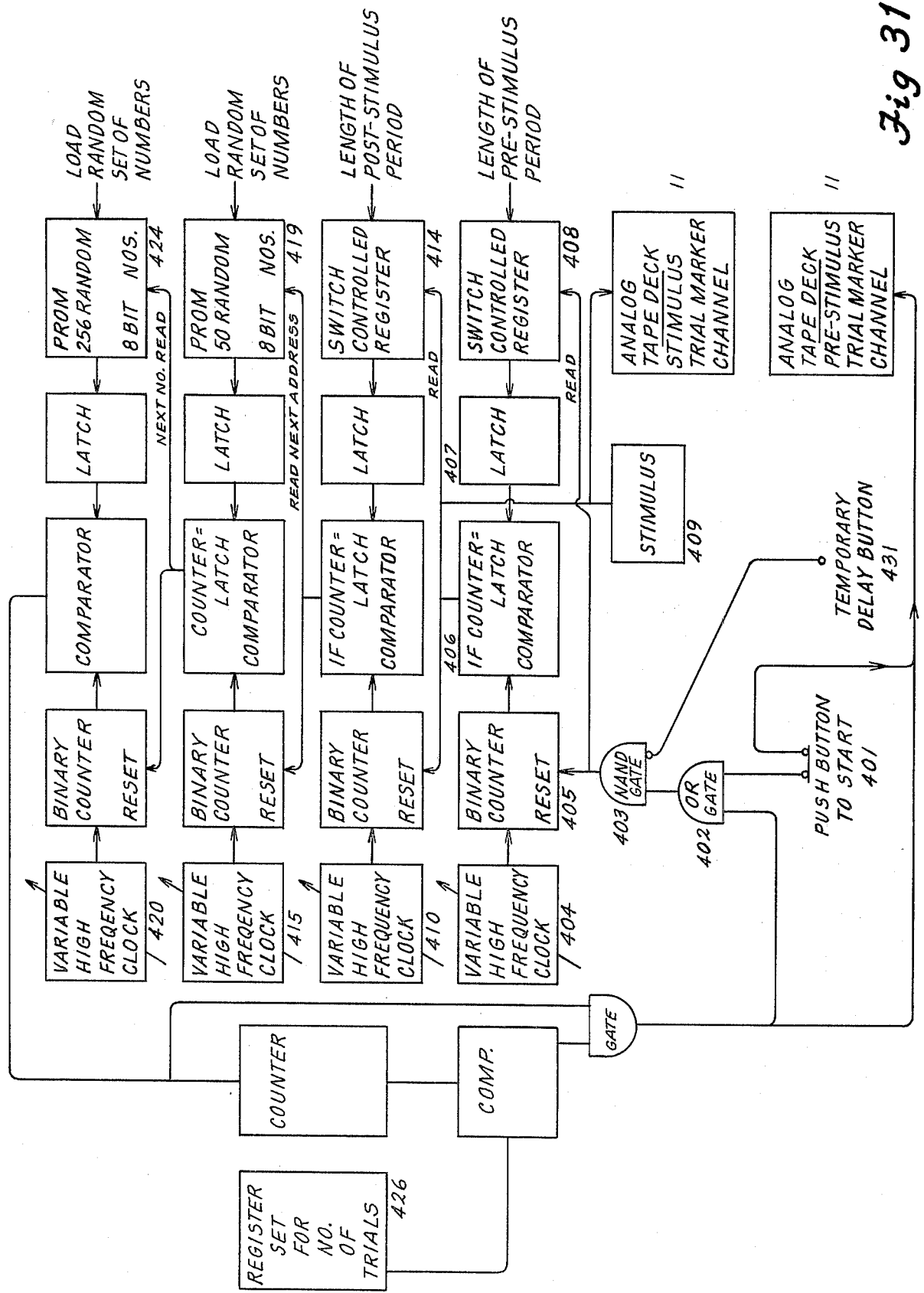
FIG. 31 is a block diagram of pseudorandom stimulus controller.

As illustrated in FIG. 31, pseurandom stimulus controller 9 comprises a four-stage timer, each stage of which in turn measures one of the four periods included in the interval between stimuli. The first stage comparator 406 measures the pre-stimulus period $p_1/f_{c1}$ where $P_1$ is a number preset by the operator in register 408 and $f_{c1}$ is the frequency set on variable frequency clock 404. When the first stage timing is completed, the second stage times the post-stimulus period as $P_2/f_{c2}$ where $P_2$ is a number preset in register 414 and $f_{c2}$ is the preset frequency on clock 410. At the end of the first stage timing period, a stimulus trial marker (5 volt spike) is recorded on the trial marker channel of tape recorder 11 and stimulus 409 is triggered. The selected post-stimulus period is long enough to permit a full decay of the transient response being observed. At the end of the second stage timing period, the third stage measures the first pseurandom time period $P_3/f_{c3}$, where $P_3$ is the next pseudorandom number in programmable read only memory (PROM) 419 and $f_{c3}$ is the preset frequency of variable clock 415. PROM 419 has been preloaded with a pseudorandom sequence of numbers. At the end of the third stage timing, the fourth stage measures a second pseudorandom period in an analogous manner based on a pseudorandom sequence in PROM 424 and a preset frequency on clock 420. When the fourth stage timing period is over, a pre-stimulus trial marker (5 volt spike) is recorded on the trial marker channel of recorder 11. A new timing cycle is then completed and the process is reiterated until the total number of transient responses recorded equals a preset number in register 426 or the process is stopped by the operator. The entire process is begun by pushing button 401, which causes the recording of a pre-stimulus trial marker. Temporary delay button 431 can be used to temporarily delay the continued operation of the timer at the operator's discretion, as for example when the subject is distracted in a manner which would render the transient response useless. A low order bit in PROM 424 or PROM 419 can be set to 0 or 1 by the operator for each number loaded into PROM 24 or PROM 19 so that two different stimuli (e.g., auditory and visual) can be triggered in a preselected order of pattern, with one stimuli being presented more frequently than the other.

The result of the recording session is an analog tape of raw EEG and EP voltage data and calibration voltages on 20 channels with trial markers on a twenty-first chanel. The next step is to load the data into computer 13.

As previously described, brain electrical activity mapping software 28 performs data collection, data manipulation, and data display functions in accordance with central information provided by the operator. The various operations can be performed in any sequence and the operator can perform a series of functions iteratively. The operator provides control information through the keyboard of terminal 22 and receives information concerning the various operations on printer 23, waveform monitor 18 and topographic color monitor 20. The flexibility of operation heightens the system's utility as a diagnostic and analytical tool.

Data Loading

Under operator control, EEG data for each brain state and related calibration signals are loaded directly onto disk storage from recorder 11 after passing through filters 12 set to pass frequency components between 0.5 and 50 Hz or between 0.5 and 1000 Hz and epileptic spike data. Gain controls on the filters are adjusted to fully utilize the signal capacity of converters 15, 16. EEG data can be sampled at rates as high as 20,000 samples per second.

Under operator control, EP data is passed through filters 12 set to eliminate frequencies above a selected frequency of between 40 and 100 Hz, or below 300 Hz for brainstem data, and is signal averaged in core memory using core averaging operation 55, which automatically rejects bad data and sets the zero baseline.

Typically EP data is sampled every 4 milliseconds, or every microseconds for brainstem analysis, and 256 samples are taken, 128 pre-stimulus and 128 post-stimulus. If the operator determines that the EP transient response data is very noisy, he may alternatively record the data as raw data and use raw data reduction operation 58 to average only selected transient response trials. In cases where the transient response data may not contain the necessary stimulus trial markers, such as in recordings of rapid eye movement (REM) sleep, the data can similarly be recorded as raw data and trail markers can be added manually by the operator, using raw data operation 58, before signal averaging is done.

Raw Data Quality Control and Display

To assure the maximum accuracy and utility of raw data, the operator can, using raw data quality control operations 56, display recorded waveforms, accept or reject each waveform for later processing, have mathematical smoothing operations performed, reset baselines or eliminate certain points of data.

The operator views the EP transient responses for the 20 channels for the purpose of evaluating the utility of each curve and specifying modifications which will improve their utility when displayed. The operator may direct a further adjustment of the baseline, which has already been set automatically, by having a constant number added to or subtracted from the value in each frame, or can determine to have the automatic baseline determination redone using a smaller number of the later pre-stimulus frames as the baseline. This procedure is particularly useful when the early pre-stimulus frames are found to contain the tail end of the transient response of the prior stimulus. By reviewing the relative levels of $V_{RMS}$ (pre-stimulus) and $V_{RMS}$ (post-stimulus) for a given channel, the operator can determine whether the background noise level is unacceptably large with respect to the transient response, necessitating another recording session with the subject. The operator may also filter any high frequency noise in the post-stimulus period by three point interpolation.

As part of the raw data quality control process, if a channel contains spurious values (e.g., voltage spikes) in particular frames, the operator can eliminate those values and substitute values interpolated from the next prior and next later frames. If the voltage levels on one channel are substantially higher than for the other channels, the operator can flag that channel to indicate that the channel should be excluded from the subsequent display scaling procedure (described below). Based on the operator's instructions, the automatic baseline determination may be redone and the results are viewed again until the operator is satisfied that the set of transient responses contain satisfactorily low noise levels and are properly zeroed.

Raw data topographic display operation 57 enables the operator to display a cartoon series of topographic maps of raw data, which has been expanded by interpolation into a matrix of 128×128 points. The cartoon can be started or stopped and run forward or reversed at will. When raw EEG data is to be cartooned, the operator can sample the data at a high rate, e.g., 400 frames per second, and then display the information at slower speed or in a series of matrices, each of which is an average of a sequence of frames. The averaging can be done on a running basis, so that the first N frames are averaged and displayed, then the N frames beginning with the second frame are averaged and displayed, and so on.

EEG Data Reduction

Raw EEG data is converted to spectral data using the fast Fourier transform process of raw data operation 58, as previously described. The segments of raw EEG curves whose spectral data is averaged are generally about 2 seconds in length each, which is shorter than the average period between spurious artifact signals. Typically from 15 to 90 segments are spectrally analyzed and the spectra averaged. The spectra usually consist of 128 frequency bands of ½ Hz in width covering the spectrum from 0 to 64 Hz. The ends of each segment can be tapered in accordance with the operators's discretion in connection with the Fourier transform process.

Reduced Data Quality Control and Topographic Display

Working with reduced EP and EEG data, that is sequences of time frames of transient response data and groups of spectral band data, the operator can use reduced data quality control operation 59 to view the waveforms, discard bad data reflecting movement artifact, eye blink, or muscle activity and eliminate high frequency noise. The reduced data can then be topographically displayed on a frame by frame or cartooned basis using the reduced data topographic display operation 60. In either case, the operator can form frames which represent combinations of underlying frames. For example, groups of ½ Hz bandwidth frames can be combined into larger bandwidth frames corresponding with typical spectra of clinical interest, e.g., alpha, beta, delta and theta. Bands of any desired width can be formed. In addition to displaying raw spectral energy information from EEG data, it is possible to display normalized spectral energy in which the points on each display are normalized to the overall spectral energy of each electrode or to the average overall spectral energy at all electrodes. In the case of EP data, it is similarly possible to display each point as a normalized value to the value at one specific electrode, e.g., the vertex electrode designated "$C_z$", or to a standardized value, or to a selected value, or to the $V_{RMS}$ of the background activity at each electrode, or to the $V_{RMS}$ of all electrodes. Similarly, the 128 frames of an EP transient response can be grouped into frames of greater time duration for display.

Group Data Analysis

By accumulating a number of stored data frames, it is possible for the operator to assemble and display group data files using group file production operation 61 and group topographic data display operation 62.

Significance Probability Mapping (SPM)

Using stored data for various groups and individuals, the operator can perform and display topographically t-statistic comparisons between groups of frames and z-statistic comparisons between an individual frame and a group of frames. Any other statistical group comparison can also be used to form a display matrix to illustrate group differences. This type of analysis, significance probability mapping (SPM), enables the operator to identify significant brain activity features related to various neurophysiological illnesses and conditions.

Grid Sector Analysis

Frames produced by the SPM procedure may be further analyzed by a Grid Sector Analysis (GSA). While the frames produced by the SPM procedure reflect regional abnormalities, the GSA procedure produces numerical measures of the degree of global or focal deviations from normal, which can assist in automatic determination of the existence of regional abnormalities in unknown subjects.

The first step in the GSA process conceptually requires the division of a frame into a number of different grids, each divided into sectors of a uniform size. Within each grid sector, the mean of all values of the data points lying within the sector is determined as the value of that sector. The process is repeated for grids of different fineness. Preferably three grids, of 4000 sectors, 64 sectors, and 16 sectors respectively, are used. Histograms of sector values are then prepared for each grid reflecting sector t-statistic or z-statistic values on the horizontal axis and numbers of sectors having that value on the vertical axis for each grid. Various analyses of the histograms, which differ for focal and global abnormalities, will indicate whether an abnormality is focal, i.e., localized in one area, or global, i.e., diffused over a large part of the brain. One such analysis would simply be the observation that the peak number of sectors for the coarser grids will be at lower z or t values in the case of a global abnormality than in the case of a focal abnormality.

In the case of focal abnormalities, there is a marked difference in the histograms for the three grids, while in the case of global abnormalities, there is little or no diffeence for the three grids. A variety of features can be developed from the histograms to serve as possible diagnostic rules. The maximum z-value for each grid, the maximum amount of asymmetry between homologous grid regions, the mean asymmetry between homologous grid regions, and the difference between the absolute values of the sum of all left hemisphere and all right hemisphere values. Also, one can calculate the number of regions above certain criterion levels for each histogram.

A group of spectral maps or a series of EP responses can be analyzed as an ensemble by forming at each matrix point the mean of the values of each map in the ensemble. The grid region on each individual map showing the largest value is given a score of 4, the next largest a score of 2, the third largest a score of 1, and the rest a score of 0. The scores are then summed by region across all maps in the ensemble, and the regions having the three largest scores and their sum are stored as indications of focal features. The same process is repeated for the three regions having the greatest asymmetries in each image between corresponding grid sectors. The resulting information can serve as features which can be processed using TICAS to develop diagnostic rules to classify unknown subjects between a group of normals and a group having a particular dysfunction. The numerical descriptors generated by GSA, when used for statistical analysis are approximately as successful in the identification of patients with brain tumors as visual inspection of EEG data by expert clinicians.

Coefficient of Variation Analysis

Given an ensemble of segments of data, the operator can determine the mean and the standard deviation of each point across the segments. By displaying the standard deviations as percentages of mean at each point, the coefficient of variation (C/V) across the skull can be observed topographically. The normal expect range of C/V values is 40-60% and deviations from that range are immediately evident from the displays. The C/V display is useful in demonstrating head regions where there are wide variations in activity, e.g., epileptogenic regions.

Difference Maps

A display matrix can be formed to represent at each point, the difference in value of corresponding points on two underlying frames. This permits, for example, displays which suggest the regions of the brain activated by patterned light, by comparing the frames corresponding to plain light stimulation and to patterned light stimulation.

Automatic Diagnostic Rules

Working from significant brain activity features and using TICAS-related operations 65, 67, 68 and 69, the operator can develop and test diagnostic rules for accurately classifying unknown subjects between normal and abnormal groups.

Scaling

Several of the available BEAM system operations produce color topographic displays. Video monitor displays typically involve assigning to each point on the display a grey tone of color which represents the value of the point. Sixteen tones of color represent 16 different graduated values. For example, red can be used for positive values and blue can be used for negative values with the grey tone of blue or red indicating the level of positive or negative value. An absence of color represents zero. In order to maximize the visual effectiveness of the display, it is desirable to scale the values of the data points to the available color tone levels in such a way that the useful variations in value are spread among the maximum range of color tones. The scaling can be done according to a variety of options. The data points can be scaled so that the maximum absolute value of the data points over a set of matrices will be equivalent to the maximum positive and negative color tones and all other points will be scaled linearly to the intermediate color tones. Scaling can be done from zero to the maximum absolute value. The same scaling technique can be accomplished with one or more channels excluded by the operator from the scaling process so that unusually high value data points will not skew the scaling process. Scaling can be done on a matrix by matrix basis rather than across a group of matrices. Scaling can be done to a maximum value chosen by the operator. In the scaling process, any data value which is larger than the brightest available grey color will be truncated and displayed as that brightest color.

Three-Point Linear Interpolation

Since the data frames to be presented for display originally contain a relatively small number of points, e.g., 20 points, and the display is preferably of a continuous matrix of 128×128 points, expansion of the data by some form of interpolation is required. The expansion is accomplished by three-point linear interpolation, in which each display point is determined as a sum of the values of the three nearest data points on the original data frame, each multiplied by a predetermined coefficient which reflects the precise location of the display point. As an alternative to the software previously described, the calculation of the display point can be done on hardware having an extremely short processing time, making possible "real-time" displays, that is, each display matrix is calculated in a time shorter than the display time for each display matrix. A detailed description of the three-point interpolation technique is contained in U.S. patent application Ser. No. 221,830 (hereby incorporated by reference).

Display Features; Multidimensional Display

Figure 32:
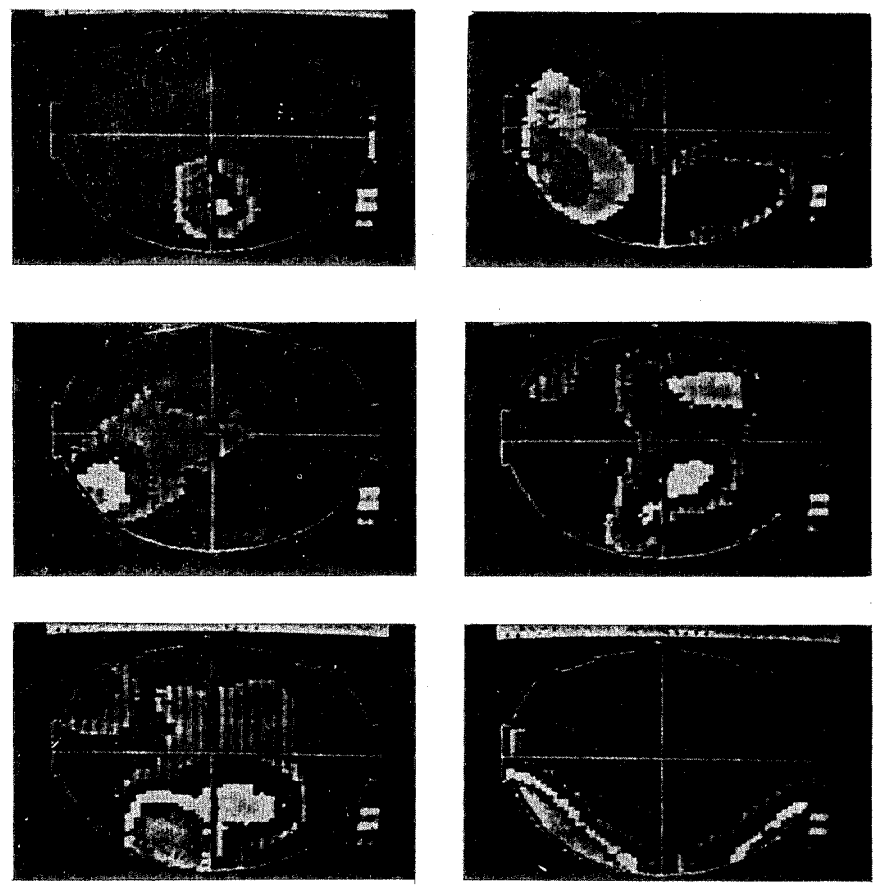
FIG. 32 is a sample of topographic displays generated by a brain electrical activity mapping system.

As illustrated in FIG. 32, the each topographic display comprises an outline of the skull with an indication of its orientation with respect to the ears and nose. All display points outside the outline are suppressed. Within the skull outline are displayed the grid of data points, each of which reflects a value or values for that point on the skull. The number of dimensions of information which may be represented by a given point varies with the display method. Frequently only one dimension of information is presented at any point in the form of a grey-tone of color on a predetermined grey-tone scale. Alternatively additional dimensions may be reflected at a point as a unique combination of three colors. Three dimensions can be represented by the quantity of each of the original colors which is mixed into the combination and a fourth dimension could be the lightness or darkness of the three. In this manner, for example, spectral EEG data for four frequency bands of brain activity could be displayed simultaneously. A detailed description of this four-dimensional display is contained in U.S. patent application Ser. No. 221,830.

Whenever displays are cartooned, the operator may select the frame rate of display from stationary to ten frames per second minimum. The cartoon can also be displayed logarithmically with time, so that the later matrices are displayed in faster sequence then the earlier ones, which visually compensates for the fact that more EP response information is available just after the stimulus than toward the end of the response period.

Examples of System Use

The brain electrical activity mapping system offers a powerful brain diagnostic and research tool by permitting immediate video display of information about steady-state brain waves, EP transient responses, spectral analyses of EEG signals, and statistical information based on these types of data, and the ability to develop diagnostic rules from selected features of data. The following examples illustrate the versatility and utility of the system.

Suspected Epilepsy

Although the "spike and wave" as seen on routine EEG graphs is virtually diagnostic of epilepsy, over 10% of all true epileptics fail to demonstrate this abnormality. Use of special electrodes, sleep studies, and activating drugs often fails to produce spikes in true epileptics. This means that although an epileptic may have brain cortex that is capable of demonstrating sufficient irritability at times to produce a seizure, that at other times it fails to be sufficiently irritative to produce a spike on the EEG and thus eludes diagnosis. Topographic display is of great assistance in such situations. Such suspected epileptic patients should have eyes open (EO) and eyes closed (EC) topographic studies performed. Irritative cortex presents itself as focal increases of activity over all frequency bands, especially the high frequency beta bands. The visual evoked EP response (VER) topographic study should also be performed. Irritative cortex leads to focal increases of both positive and negative waves. If the epilepsy is associated with an atrophic lesion, a region of reduced EEG and EP activity may be found in close association with the focal irritability.

When spikes are found, displays of their topographic extent are extremely useful in determining their point of origin. In this case, raw EEG data is displayed in cartoon form thus delineating the epileptic dipole.

Suspected Supratentorial Brain Lesion

Patients are often referred for EEG tests in order to rule in or out a lesion of one or both cerebral hemispheres. This includes tumor, stroke, abscess, atrophy, arterio-venous malformation, congenital malformation, hemorrhage, regional encephalitis. These subjects should be subjected to topographic studies in the eyes open and eyes closed brain states, and for the VER and bilateral semotosensory evoked response (BSER) EP situations. In general these lesions may be recognized by the pattern of hypo- or hyperactive cortex that become visible on the brain electrical activity mapping images. For example, tumors show decrease in activity early, excessive activities later, and reduced activity at the vertex. Brain electrical activity mapping greatly adds to the information obtained by radiographic scanning as it is sensitive to the functional disturbances produced by these lesions which usually extend beyond the anatomical limits of the lesion.

To pinpoint abnormalities the techniques of significance probability mapping (SPM) should be used. Furthermore, quantification of a lesion by grid sector analysis (GSA) is often useful.

Brain electrical activity mapping is most useful when tests must be applied to a large population for screening purposes or repeatedly to a single person. Such uses would include screening for tumor and stroke, determining whether a lesion is increasing or decreasing, and assessing the effects of treatment on a lesion. Brain electrical activity mapping is completely non-invasive, and not dangerous as radiographic techniques would be in such circumstances. There is also evidence that many lesions produce electrical (functional) disturbances before they can be detected by radiographic means.

Suspected Learning Disabilities

Brain electrical activity mapping studies are most useful in the elucidation of regional abnormalities of brain activity found in dyslexia, hyperactivity, dyscalculia, and combinations of the above. For example, dyslexia reveals abnormalities not just in the classic left temporal lobe speech areas but in the medial frontal lobe bilaterally. To demonstrate these abnormalities, one needs to perform the full test battery which includes: right hemispheric activating tests (the Kimura Figures task and listening to music as described elsewhere); left hemispheric activating (listening to speech and reading Grey Oral passages as described elsewhere); and bi-hemispheral tests (Paired Associates test and the Tight-Tyke evoked potential phenomic discrimination test as described elsewhere).

Automated classification tests to discriminate among these clinical entities can be developed.

Emotional Dysfunction

Many forms of emotional disorder can be caused by the lesions mentioned above. Brain electrical activity mapping can be more useful in the recognition of covert pathology in this patient population than radiographic techniques. In addition, certain forms of psychopathology have recognizable brain electrical activity mapping signatures. For example sociopathic behavior is associated with lack of synchrony between the frontal lobes; e.g., the VER may show different electrical polarity between the right and left frontal lobes. Schizophrenia shows markedly increased EEG slow activity overlying the frontal regions. In this group of subjects, the eyes open and eyes closed EEG and VER studies are most useful.

Infant Competence

Discrimination between babies at risk for future learning and emotional problems is a frequent clinical request. Brain electrical activity mapping has proven useful in accomplishing such discrimination. In addition to studying the EEG and VER in stages 1 and 2 sleep, the EEG should be studied while the babies are brought into the alert state and maintained there as discussed elsewhere. Less competent babies, for example, show paradoxical increases in frontal delta slowing as they are alerted.

Suspected Dementia

Senile and pre-senile dementia represent a major problem for gerontologists and neurologists. Radiographic evidence of brain abnormality may not be found until the clinical symptom complex is well established. On the other hand, brain electrical activity mapping studies demonstrate early abnormalities in a non-invasive manner. The best battery of tests is similar to those described above for suspected learning disabilities, but generally the tight-tyke EP is replaced by another EP where the subject must discriminate between frequently and infrequently heard tone pips of differing frequency. A difference EP between the response to the two different tone pips is produced. The topographic display of the difference EP shows a marked reduction in dimentia and may be used to follow the course of dementia and the response of dementia to pharmacotherapies.

Headache

Headache may be caused by many factors. Brain electrical activity mapping is very useful to screen out serious lesions of the types described as supratentorial lesions above. The specific syndrome of migraine headache has a frequently seen pattern on brain electrical activity mapping of excessive 8–11 Hz occipital oscillations and excessive occipital activity. It is best to use the EO and EC EEG and VER for headache. Occasionally the BSEP is useful.

Comparison of Individual to Group

As described above, the brain electrical activity mapping system is generally able to compare an individual statistically to a group and display the result topographically. In a clinical setting, the individual in question, who may have displayed a normal CT scan, is compaared to an age matched/sex matched group of normals, and abnormalities are then displayed in colormapped form, wherein bright colors show high abnormality and dull colors show insignificant abnormality. This technique provides an effective diagnostic tool.

Comparisons of Groups; Automatic Diagnosis Rules

The result of a group comparison under the system is a topographic display of statistical difference expressed as t-statistics, which when coupled with the number of degrees of freedom available in the calculation, produce a probability level of significant difference between two groups at a particular brain state. For instance, a group of normals could be compared to a group of schizophrenics by the creation of t-statistic displays with respect to a variety of brain states and stimuli. The user looks for displays which exhibit high degrees of coherence and statistical difference. This is normally shown on a screen in color. The larger statistical differences appear as brighter colors. The degree to which the differences are focused at particular points or diffused over the skull is also apparent. Smoothness in the lines dividing areas of different brightness suggests focused differences, while diffuse differences are suggested by ragged edges between dim and bright areas. It is possible for the researcher, upon selection of a particular map that shows something interesting, to save the matrix for later analysis. Such a saved matrix of t-statistics can be used to non-linearly weight the underlying data frames to create features which can be analyzed using TICAS. Once a set of saved frames representing group difference information is accumulated, he then converts all of the saved information, representing features which tend to distinguish the two groups into a file format which is suitable for analysis by TICAS, which is a multi-variate classification system, publicly available from the University of Arizona, courtesy of Dr. Peter H. Bartell.

TICAS is designed to sift through all of the features saved in the course of the inter-group analysis and pick those which prove to be the most discerning mathematically to produce a set of features which succinctly allows automatic diagnosis of a patient.

This procedure has been used to successfully discriminate between normal subjects and those with dyslexia, to discriminate between normal subjects and those with supertentorial brain tumor, and to discriminate between subjects with exposure to organophosphate compounds and nonexposed controls.

Dyslexia Analysis

An article, *Dyslexia Regional Differences in Brain Electrical Activity by Topographic Mapping*, Duffy et al. (Annals of Neurology, Vol. 7, No. 5, May, 1980), hereby incorporated by reference, describes the use of the brain electrical activity mapping system to identify the parts of the brain whose electrical activity differs for individuals suffering from reading disability (dyslexia) as compared with normal individuals, and to establish objective standards for diagnosing dyslexia. The previously described battery of brain state tests were administered to a dyslexic group and a control group. Visual and auditory stimuli were repeatedly presented to both groups and recorded with the appropriate trial markers. The stimuli were offered in pseudorandom fashion. Using the brain electrical activity mapping system, topographic displays of the alpha (8 to 11.75 Hz) and theta (4 to 7.75 Hz) activity at each electrode for each tested brain state for each subject were produced. Similar cartoons of 128 frames (4 milliseconds each) were prepared for each type of EP response for each subject. The resulting brain state frames and EP response frames for the dyslexic group and the control group were then averaged to form mean frames of each group for each state and stimulus. The two groups of means images were then compared using the t-statistic function. A further transformation produced a matrix of percentile index values (PI) whose value is related inversely to t-values. The PI values permit a graphic localization of regions of maximum difference between the dyslexic group and the control group. By topographically displaying the PI matrices for alpha and theta for each brain state and for each EP stimulus, it was possible to identify the brain regions which differed between the dyslexics and the controls. As a final step, a new display matrix was formed which summarized the differences reflected in all of the PI matrices as indicated by the occurrence of a certain PI level on at least one of the underlying PI matrices. The map of PI differences having a value of at least 2 identified four brain areas related to dyslexia: (1) bilateral medical frontal, (2) left anteriolateral frontal, (3) left mid-temporal and (4) left posterolateral quadrant. Classic concepts of dyslexia had not suggested the involvement of all of these brain areas in dyslexics. The study also indicated that alpha brain activity was involved in dyslexia as well as the theta activity which has previously been viewed as of primary importance.

In *Dyslexia: Automated Diagnosis by Computerized Classification of Brain Electrical Activity*, Duffy et al. (Annals of Neurology, Vol. 7, No. 5, May, 1980) hereby incorporated by reference, specific highly effective diagnostic rules for identifying dyslexics were developed by a rule selection process applying TICAS software to the brain wave data derived in the study described immediately above. Working from displays of brain electrical activity, 183 features were identified for particular regions and brain states in which the strongest differences between the dyslexic group and the normal group occurred. Two of the 183 features were identified as capable of classifying unknown subjects as dyslexic or normal with a success of 80-90%.

Localization of Tumor

In *Brain Electrical Activity Mapping (B.E.A.M.); A Method for Extending the Clinical Utility of EEG and Evoked Potential Data*, Duffy, et al (Annals of Neurology, Vol. 5, No. 4, April, 1979), hereby incorporated by reference, the use of brain electrical activity mapping system topographic displays to identify the location of a brain tumor was discussed. Spectral EEG data in the four classic bands (delta, theta, alpha, and beta) was recorded for various tested brain states. Average EP response data for strobe light stimuli comprising 128 time frames of 4 milliseconds each was also recorded. After three-point linear interpolation to expand the matrix, displays of spectral EEG data, and cartooned EP data were obtained. FIG. 5 of the article illustrates the spectral EEG displays in the four classic bands of brain activity for a patient with a known tumor, which had been located by CT scanning. The assymmetries in the spectral displays also identify the area of the tumor, although the suggested lesion size was larger than indicated by CT scanning. Analysis of 7 tumor patients, whose classic EEG's were normal or non-localizing, showed that brain electrical activity mapping studies were able to define the lesions almost as effectively as CT scan.

Use of Significance Probability Mapping with B.E.A.M. to Compare Groups and Compare Individuals to Groups In *Significant Probability Mapping: An Aid in the Topographic Analysis of Brain Electrical Activity*, Duffy et al., accepted for publication (hereby incorporated by filing a copy thereof as an Appendix) the authors describe the use of topographical displays of statistical transformations of data. In one application, EP response data was obtained from a group of subjects with brain tumors and a second control group of subjects. The data was broken into sequential frames of 4 milliseconds each. For the control group, new matrices of mean and variance of each electrode over all members of the group were prepared. A z-statistic matrix was formed for each tumor subject to illustrate his deviation from the normal population. Using the z-statistic display a clinical neurophysiologist was able to identify 11 of 12 tumor subjects.

In a second application, discussed in the same article, EEG steady-state signals were recorded for three different brain states (resting but alert with no external stimulation, listening to a tape recording of speech, and listening to a tape recording of music) for individuals in a group of dyslexics and individuals in a group of normal readers. Matrices of alpha band activity were produced for each individual, and mean and variance matrices for each state were prepared for each of the two groups. For each group t-statistic matrices were formed to compare the resting and listening to speech states and the resting and listening to music states. By examining the t-statistic displays for the two groups it was possible to infer the differences in speech-induced and music-induced brain activity between the dyslexics and the normal readers. Those determinations could not have been made from an analysis of the underlying EEG alpha matrices.

Use of Grid Sector Analysis of B.E.A.M. SPM Data to Determine Degree of Focal or Global Deviation From Normal In an unpublished article, "Quantification of Focal Abnormalities in BEAM Data by Grid Sector Analysis: Automated discrimination Between Normal Subjects and Patients with Superatentorial Brain Tumor", Duffy, et al., (hereby incorporated by filing a copy thereof as an Appendix) describes uses of grid sector analysis as part of the brain electrical activity mapping system for the purpose of automated neurophysiological diagnosis of brain tumor. In this application, EEG and visual EP data were recorded from a group of patients with confirmed supratentarial brain tumor and from a control group. SPM matrices were prepared comparing the tumor subjects to a normal group and comparing the control group to the tumor group. Four 96 millisecond time periods of EP data were analyzed. Grid sector analyses on the data resulted in a set of 1096 combined global and focal features from the combined EEG and EP data. By a process of features selection and rule development and testing, two features were identified as most useful in distinguishing the tumor subjects from the control subjects. When classification rules developed on the initial group of 30 subjects were applied to a new group of 10 subjects, containing 5 normals and 5 subjects with brain tumor, all ten were correctly classified.

Other Embodiments

Other embodiments of the invention are within the following claims. For example, the input data may be obtained from any type of transducer capable of measuring brain electrical activity, and topographic displays can be prepared from the signals taken from the skull, without interpolation of additional points to form a display matrix.

Related Applications

This application is related to the following applications, each of which is hereby incorporated by reference:

(1) Frank H. Duffy and Norman David Culver, Brain Electrical Activity Mapping (BEAM)
(2) Frank H. Duffy, Brain Electrical Activity Mapping (BEAM)
(3) Norman David Culver, Analysis of Brain Electrical Activity
(4) Norman David Culver, Apparatus and Method for Topographic Display of Multichannel EEG Data, U.S. Ser. No. 221830.

What is claimed is:

1. Apparatus for generating a topographic display of information on the electrical activity of the brain, said apparatus comprising a plurality of electrical-activity transducers adapted to be placed at spaced apart locations on the skull of a patient, processing means connected to be responsive to said transducers to generate a time sequence of response matrices, the elements of each said response matrix representing the instantaneous amplitudes of responses of said transducers at various locations on the skull, said processing means including means to generate from said time sequence of response matrices a succession of running-average matrices each corresponding to an average of a plurality of successive response matrices in said sequence, at least two of said running-average matrices corresponding respectively to two averages which include in common at least one of said response matrices, display means connected to be responsive to said processing means, for displaying said running-average matrices as a time sequence of topographic maps of the skull, the elements of said running-average matrices defining discrete points of said maps.

2. Apparatus for generating a topographic display of information on the electrical activity of the brain, said apparatus comprising a plurality of electrical-activity transducers adapted to be placed at spaced apart locations on the skull of a patient, sampling means connected to be responsive to said transducers, for sampling responses measured at said transducers and storing the response samples as a series of data matrices, one matrix for each sample taken, processing means connected to be responsive to said dampling means, for processing said data matrices to generate one or more processed matrices, interpolation means connected to be responsive to said processing means, for generating one or more expanded matrices by expanding the number of elements in said processed matrices to provide elements corresponding to skull locations intermediate said transducer locations, said interpolation means including means for storing three predetermined interpolation coefficients for each new matrix element to be generated by interpolation, said coefficients corresponding to the skull location of said new matrix element with respect to the three closest transducer locations, means for generating each said new matrix element by multiplying said coefficients by the existing elements of said processed matrix corresponding to the three closest transducer locations and summing the three products, display means for displaying said expanded matrices as topographic maps of the skull, said matrix elements forming discrete points of said maps.

3. A method for generating a topographic display of information on the electrical activity of the brain, said method comprising the steps of placing a plurality of electrical-activity transducers at spaced apart locations on the skull of a patient, processing responses at said transducers to generate a time sequence of response matrices, the elements of each said response matrix representing the instantaneous amplitudes of said responses at various locations on the skull, said processing step including generating from said time sequence of response matrices a succession of running-average matrices each corresponding to an average of a plurality of successive response matrices in said sequence, at least two of said running-average matrices corresponding respectively to averages which include in common at least one of said response matrices, displaying said running-average matrices as a time sequence of topographic maps of the skull, the elements of said running-average matrices defining discrete points of said maps.

4. A method for generating a topographic display of information on the electrical activity of the brain, said method comprising the steps of placing a plurality of electrical-activity transducers at spaced apart locations on the skull of a patient, sampling responses measured at said transducers and storing the response samples as a series of data matrices, one matrix for each sample taken, processing said data matrices to generate one or more processed matrices, generating one or more expanded matrices by expanding the number of elements in said processed matrices to provide elements corresponding to skull locations intermediate said transducer locations, said generating step including storing three predetermined interpolation coefficients for each new matrix element to be generated by interpolation, said coefficients corresponding to the skull location of said new matrix element with respect to the three closest transducer locations, generating each said new matrix element by multiplying said coefficients by the existing elements of said processed matrix corresponding to the three closest transducer locations and summing the three products, displaying said expanded matrices as topographic maps of the skull, said matrix elements forming discrete points of said maps.

* * * * *